(12) United States Patent
Tao

(10) Patent No.: US 6,610,005 B1
(45) Date of Patent: *Aug. 26, 2003

(54) CATHETER SYSTEM FOR IMPLANTING EMBRYOS

(76) Inventor: Jun Tao, 5333 W. Mercury Pl., Chandler, AZ (US) 85226

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/542,060

(22) Filed: Apr. 3, 2000

Related U.S. Application Data

(63) Continuation-in-part of application No. 09/010,876, filed on Jan. 22, 1998, now abandoned, which is a continuation-in-part of application No. 08/638,451, filed on Apr. 26, 1996, now abandoned.

(51) Int. Cl.[7] ................................................. A61D 7/00
(52) U.S. Cl. ............................... 600/34; 600/33; 604/3; 604/194; 604/197; 604/198; 604/200
(58) Field of Search ............................... 600/33, 34, 35; 604/1–3, 93.01, 181, 184, 192, 197, 198, 199, 200, 263

(56) References Cited

U.S. PATENT DOCUMENTS

| | | | |
|---|---|---|---|
| 3,507,281 A | * | 4/1970 | Cassou ........................ 604/232 |
| 3,513,830 A | | 5/1970 | Kalayjian |
| 4,249,536 A | | 2/1981 | Vega |
| 4,457,313 A | * | 7/1984 | Alter ........................... 600/562 |
| 4,865,589 A | | 9/1989 | Simmet et al. .............. 604/171 |
| 6,010,448 A | | 1/2000 | Thompson .................... 600/34 |
| 6,368,302 B1 | * | 4/2002 | Fitzmaurice et al. ... 604/102.01 |

OTHER PUBLICATIONS

International Search Report issued in connection with PCT/US01/1022.

* cited by examiner

Primary Examiner—Rosiland S. Kearney
(74) Attorney, Agent, or Firm—Schmeiser, Olsen & Watts LLP

(57) ABSTRACT

Described is a catheter system for implanting embryos into a woman's uterus. The catheter system utilizes a protective catheter sleeve for introducing a catheter into the uterus without mucus contamination of an inner catheter. Once the sleeve containing the inner catheter is introduced into the uterus, the protected inner catheter, carrying the embryos, is pushed through a swivelable distal end cap on the sleeve to a desired implanting location. The distal end of the inner catheter has a protective cap and a side opening for embryo release. Also, stiffness and indicia features of the outer sleeve and inner catheter assist in the physician's handling of the catheter system and in ensuring a desired uterus location for implanting.

69 Claims, 6 Drawing Sheets

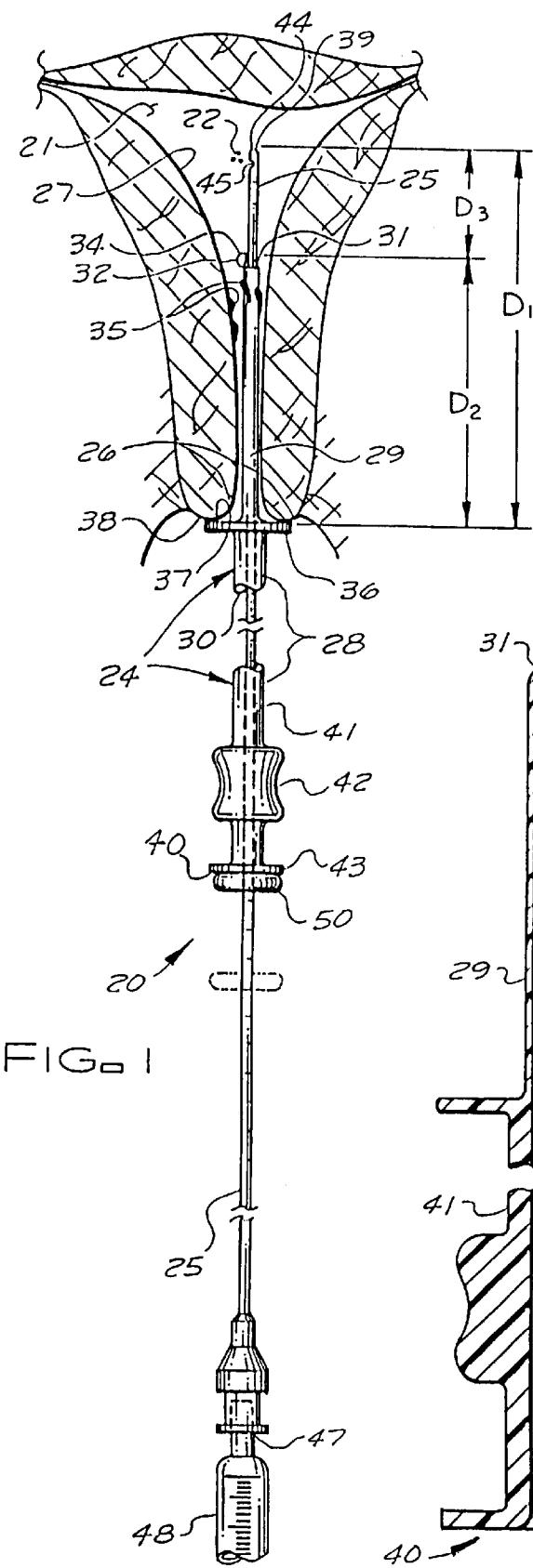
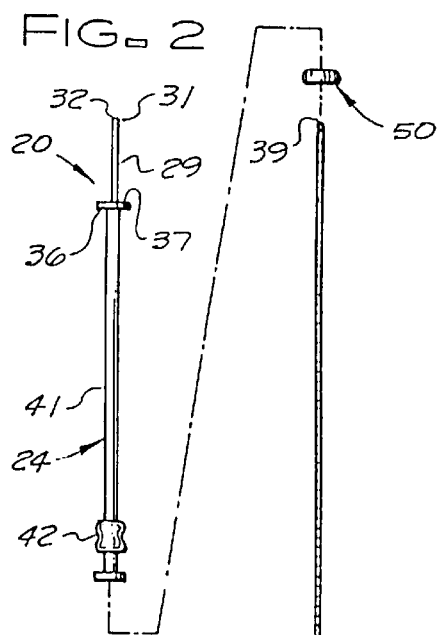
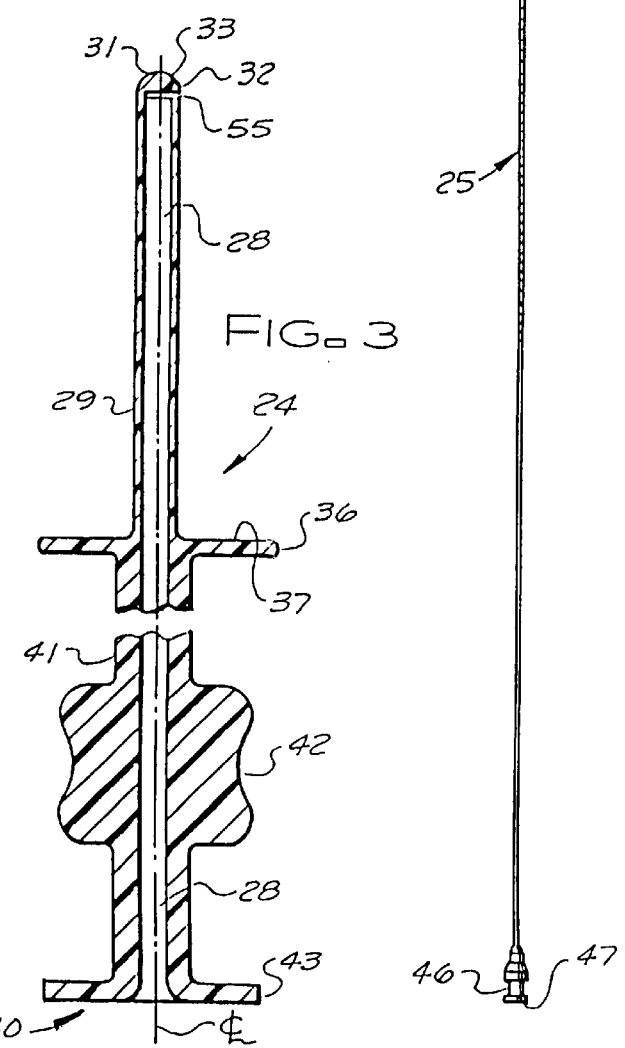
FIG. 1
FIG. 2
FIG. 3

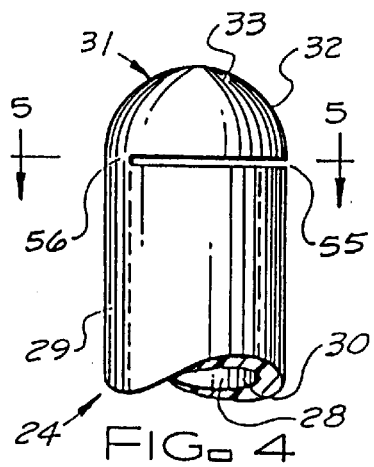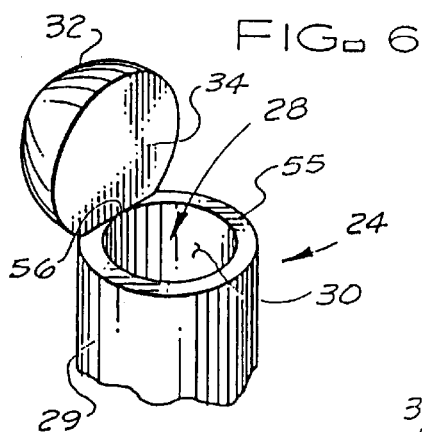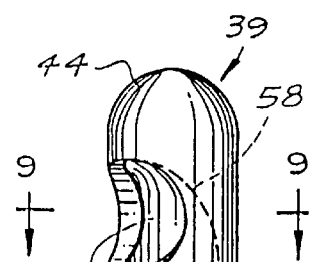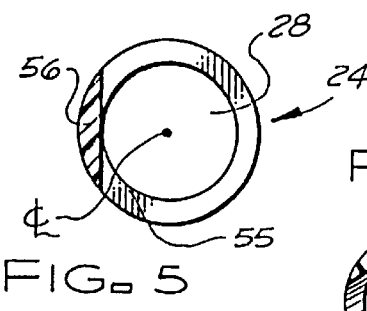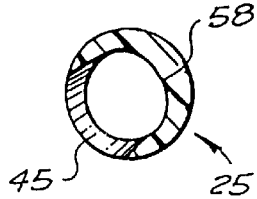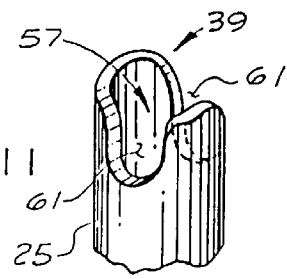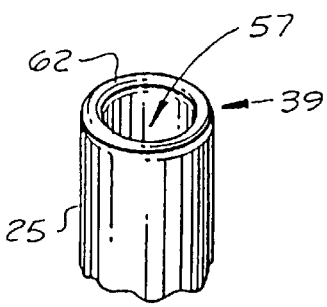

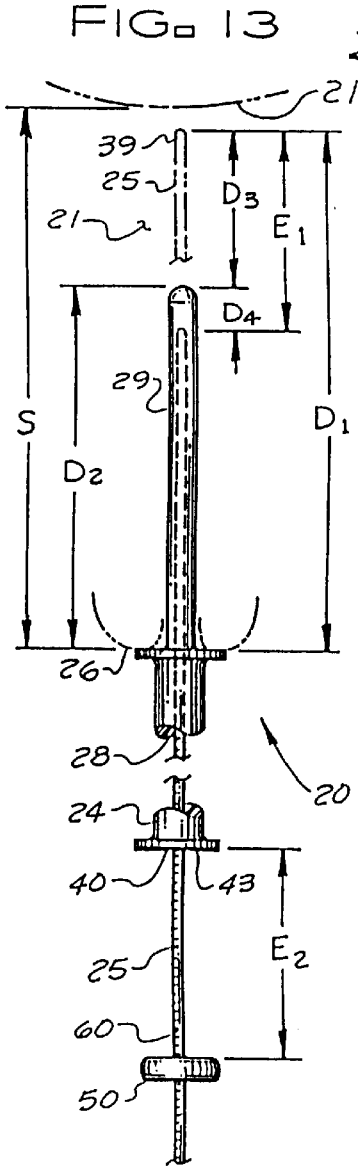
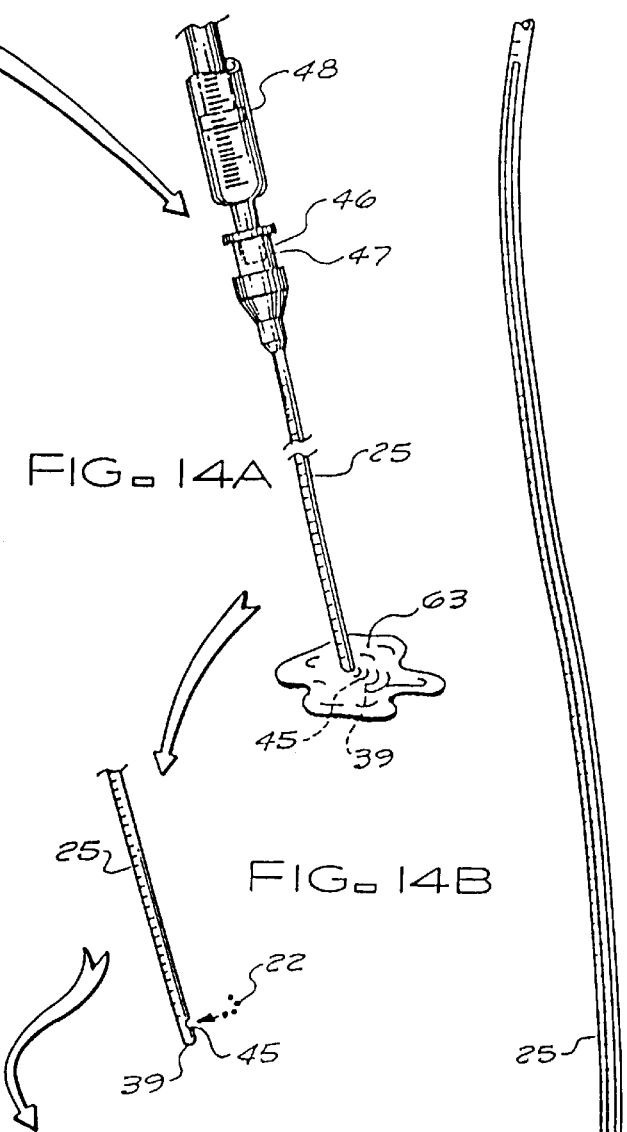
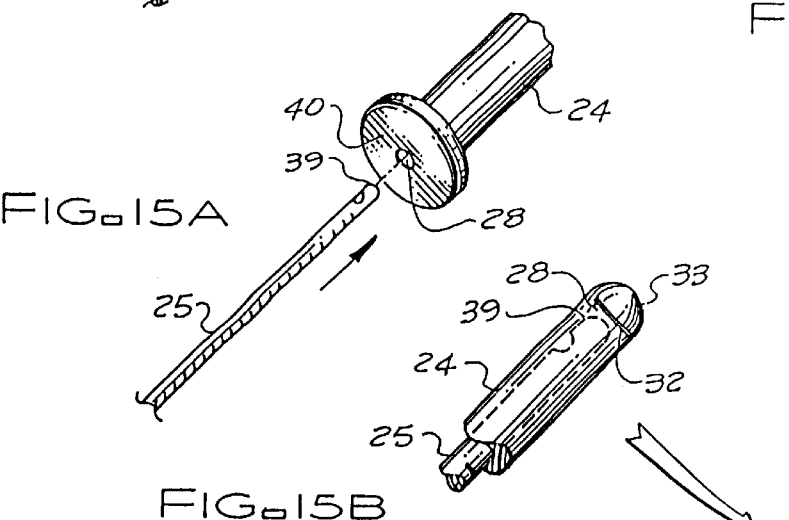

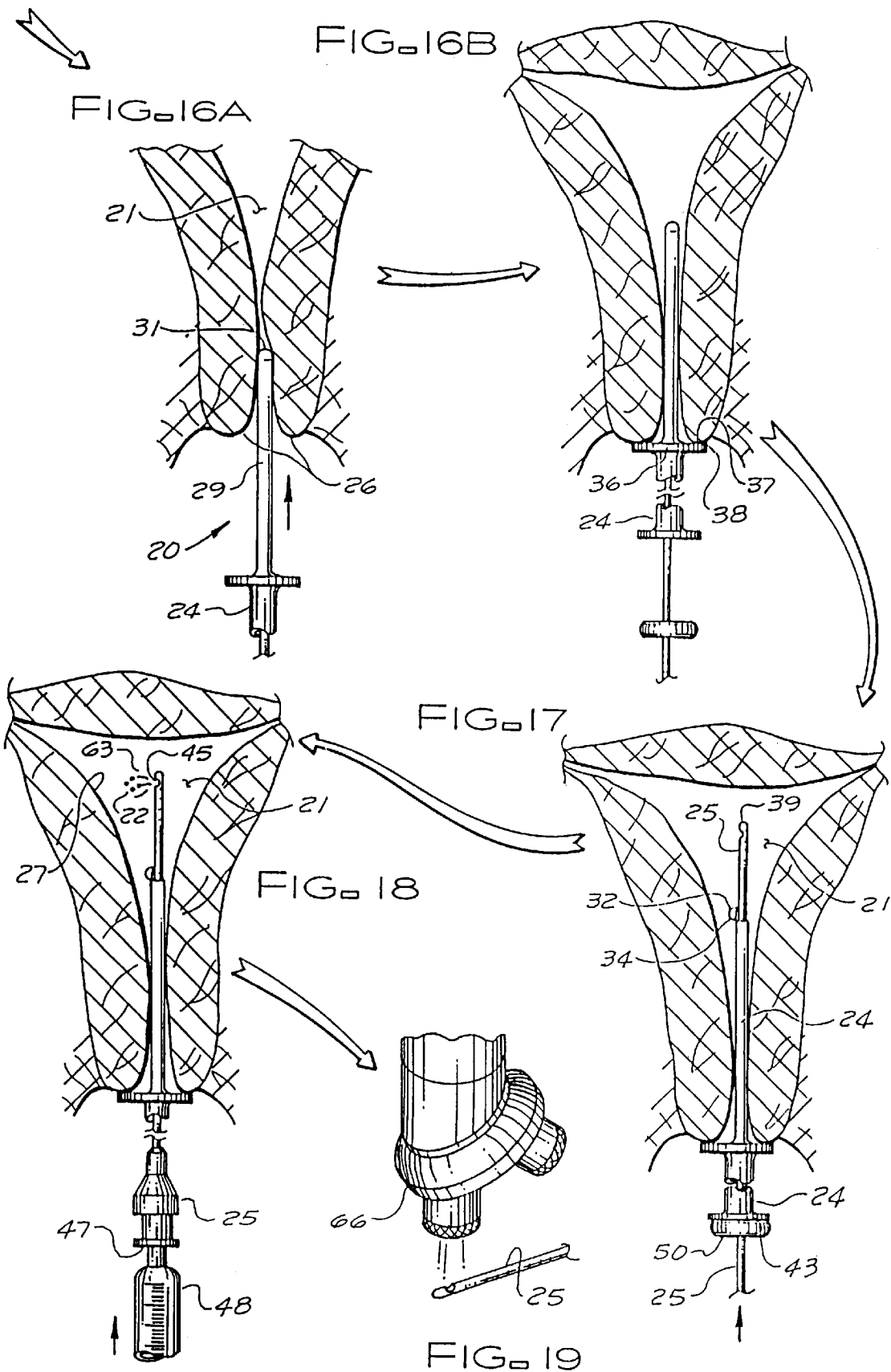

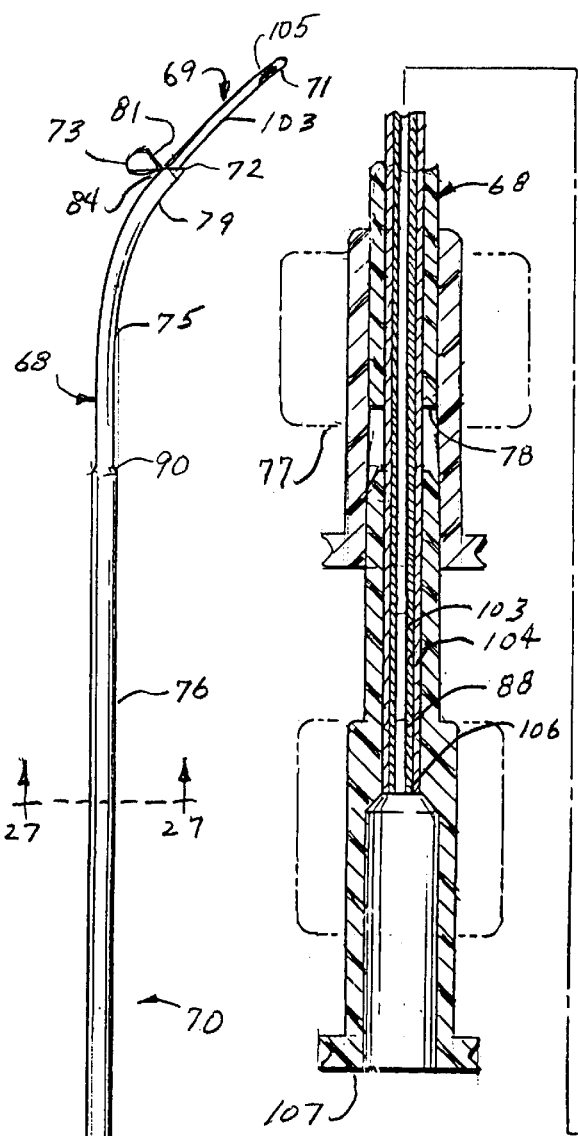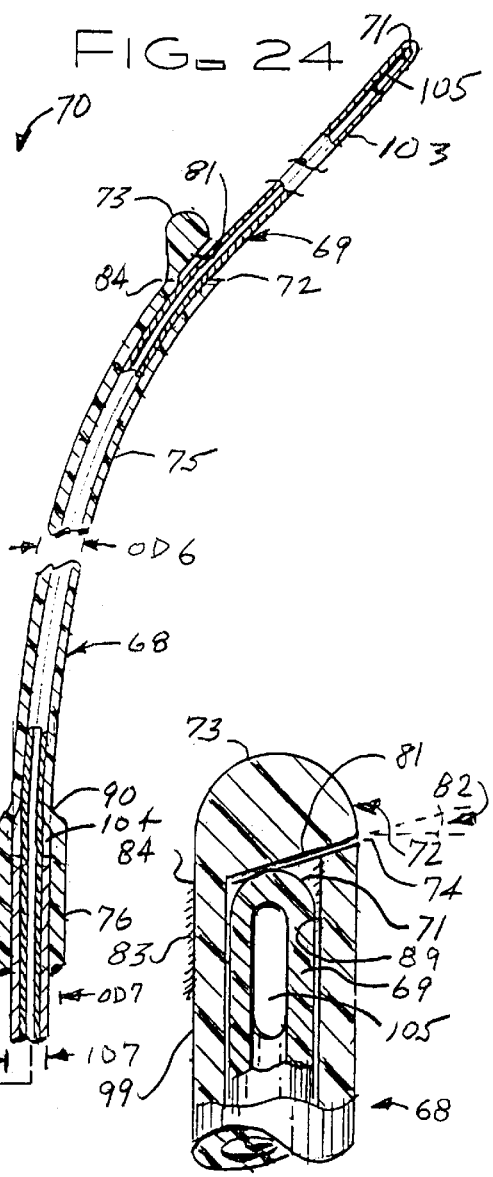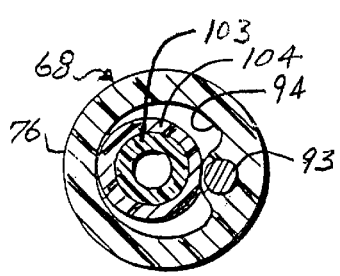
FIG. 23  FIG. 24  FIG. 25  FIG. 26  FIG. 27

CATHETER SYSTEM FOR IMPLANTING EMBRYOS

CROSS REFERENCE TO RELATED APPLICATION

The present application is a continuation-in-part of U.S. application Ser. No. 09/010,876 filed Jan. 22, 1998, abandoned in favor of this application, which first application was a continuation-in-part of U.S. application Ser. No. 08/638,451 filed Apr. 26, 1996, now abandoned.

BACKGROUND OF THE INVENTION

1. Field of the Invention

The invention relates to a catheter system for implanting embryos into a woman's uterus. More particularly, this invention concerns such a catheter system utilizing a protective catheter sleeve for introducing a catheter into the uterus without mucus contamination. And it concerns an improved catheter construction for embryo protection and deposit.

2. Description of the Prior Art

Typically, in present fertility clinics, three or four embryos are placed in a tiny, flexible catheter near the opening in the depositing end (the distal end) of the catheter. The catheter is then inserted through the woman's cervix and the embryos flushed hydraulically from the catheter and, hopefully, the embryos become implanted in the uterus wall. But the small catheter required is difficult to insert and mucus from the mouth of the cervix may be caught at the mouth of the catheter and interfere with the embryos. So, a stiffer and larger sleeve catheter may be used for insertion through the cervix; and then the smaller catheter may be pushed through and out the larger sleeve catheter to implant the embryos. This sleeve use helps, but cervix mucus may still be caught in the introduction end (the distal end) of the larger catheter and then transferred to the smaller catheter, thus still possibly interfering with the embryos.

The prior art includes some catheter-type devices for use in embryo implantation. In particular, Bacich U.S. Pat. No. 5,472,419 and Fischl U.S. Pat. No. 4,790,814 both employ the use of a catheter-type device, each having distal end openings to allow passage of the embryos to the uterus. Though these devices may be used for embryo implantation, they do not adequately address the problem of preventing the accumulation of mucuslike material at the distal end opening, which may interfere with embryo implantation. Other embryo implanting devices employ the use of a catheter enclosed within an outer sleeve. For example, Wallace's GB No. 2,118,840 employs the use of an inner catheter slidable within an outer sleeve where the distal end of the outer sleeve is open. Though this device might also be suitable for embryo implantation, it fails to teach or implement an efficient way to protect against mucus accumulation within the outer sleeve during insertion. Other medical devices in fields other than embryo implantation employ the use of a catheter enclosed within an outer sleeve. For example, Pokorney U.S. Pat. No. 5,083,572 employs the use of an inner catheter slidable within an outer sleeve for use in obtaining vaginal secretions; but the purpose and construction are to bring in secretions/mucus within the outer sleeve, not to keep them out. And Pokorney's use of side sampling ports near the distal end of the outer sleeve do not prevent mucus accumulation within the outer sleeve nor does the sleeve permit the inner catheter to slide out of the sleeve to deposit an embryo or for any purpose whatsoever.

Other background art, still further removed from addressing such problems as mucus accumulation during embryo implanting include Kalayjian U.S. Pat. No. 3,513,830, which discloses an instrument for obtaining body cultures. This instrument employs the use of a cotton swab slidable within a plastic sterilizable outer sleeve. The outer sleeve has a friction-fitted cap, outwardly convex, which can be inserted into a body cavity closed and then opened once inside the desired cavity to allow the cotton-tipped swab to project out of the outer sleeve to take a tissue sample. An object of the Kalayjian invention is apparently to prevent the swab from becoming contaminated either before or after the swab comes in contact with the desired tissue. Kalayjian differs from the present invention in many ways: it is not designed for the purpose of embryo implanting; it is not designed to hold an inner catheter (it holds a wooden swab); it is not designed to be "opened" by a fragile inner catheter (and might well destroy an emerging inner catheter); the cap/tip is deigned (internally indented) to match the swab; etc. O'Neil, U.S. Pat. No. 4,652,259, is even further afield. It discloses a.urinary catheter assembly and has to do with bacteria protection of the bladder in collecting urine, not mucus and embryo protection for transplanting. The sleeve is built for specific use only in the outer urethra and only the inner catheter is permitted to travel alone through the inner urethra and into the bladder for catheterization. Similarly, Vega, U.S. Pat. No. 4,249,536, discloses a urological catheter with a soft pliable cone-shaped tip (containing spiral grooves or hair-like projections) which can open by means of strings attached to the tip. This device also uses magnetic forces to advance the catheter through the urethra. This device differs in many important ways from the present invention; e.g., the Vega tip opens to a very wide position which could cause significant trauma if used for embryo transfer; the Vega device uses strings to pull open the tip of the catheter, and the tip itself is not a unitary small, light, part of the distal end of the catheter, openable by the pushing of a fragile embryo-transfer type of inner catheter, etc.; and closing such a device is difficult. Whatever end system may be used on a sleeve for embryo transfer, it is obviously vitally important that pieces of the end do not break off and remain in the cervix.

Thus there is a need for a catheter system for implanting embryos which will better protect the embryos from mucus and other damage in an efficient manner.

OBJECTS OF THE INVENTION

A primary object of the present invention is to fulfill the above-mentioned needs by the provision of an improved catheter system for implanting embryos. A further primary object of the present invention is to provide such a catheter system which is efficient, inexpensive, and handy. Other objects of this invention will become apparent with reference to the following invention descriptions.

SUMMARY OF THE INVENTION

According to a preferred embodiment of the present invention, this invention provides a catheter system for assisting implanting embryos in a uterus, comprising: catheter sleeve means, having a sleeve distal end and a sleeve proximal end and having, between such sleeve distal end and such sleeve proximal end, a longitudinal cylindrical hollow having a central longitudinal axis, such catheter sleeve means being structured and arranged for containing an inner catheter in such cylindrical hollow, such catheter sleeve means comprising end cap means, disposed along an intersection of such central axis at such sleeve distal end, for substantially enclosing such cylindrical hollow at such sleeve distal end to protect such cylindrical hollow from accumulating mucuslike material when such catheter sleeve means is pushed through a cervix, such end cap means comprising end opening means, disposed along such intersection of such central axis at such sleeve distal end, for permitting passage of an inner catheter along such central axis from within such cylindrical hollow into a such uterus; such catheter sleeve means being structured and arranged for travel of such sleeve distal end through the cervix for assistance in implanting embryos.

Further, this invention provides such a system wherein such end opening means of such sleeve distal end comprises swivel means constructed and arranged in such manner that such end cap means swivels outward when an inner catheter is pushed through such sleeve distal end; and, further, wherein such end cap means comprises an outwardly convex flexible end on such catheter sleeve means and such end cap opening means comprises a partial transverse cut separating, except for a remaining transverse hinge portion, such outwardly convex flexible end from such catheter sleeve means, whereby such end cap means is constructed and arranged to swivel outward when an inner catheter is pushed through such sleeve distal end. And it provides such a system further comprising: an inner catheter means, having a catheter distal end and a catheter proximal end, for transporting a such embryo through such cylindrical hollow of such outer sleeve means into access to such uterus and for depositing such embryo in such uterus; and, further, wherein such inner catheter means comprises indicia means for indicating longitudinal distance to assist in attaining a desired implanting location.

Also, this invention provides such a system wherein such catheter distal end comprises: catheter distal opening means for depositing such embryo, such catheter distal opening means comprising a side port, adjacent such catheter distal end of such inner catheter means. And it provides such a system wherein such catheter distal end comprises: second end cap means at such catheter distal end for protecting such inner catheter means when such catheter distal end is pushed through such sleeve distal end; and catheter distal opening means for depositing such embryo, such catheter distal opening means comprising a side port adjacent such second end cap means at such catheter distal end of such inner catheter means; and, further, wherein such catheter distal end further comprises strengthening means opposite such catheter distal opening means for strengthening such inner catheter means against breakage. Also, it provides such a system wherein such end opening means at such sleeve distal end of such catheter sleeve means comprises swivel means constructed and arranged in such manner that such end cap means swivels outward when such catheter distal end is pushed through such sleeve distal end.

In addition, it provides such a system wherein such catheter sleeve means further comprises first stop means for limiting insertion to a desired location when such catheter sleeve means is inserted through the cervix; and, further, wherein such inner catheter means further comprises second stop means settable along such inner catheter means for limiting insertion to a desired implanting location when such inner catheter means is inserted into a such uterus. And it provides such a system wherein such catheter sleeve means further comprises stop means for limiting insertion to a desired location when such catheter sleeve means is inserted into a such uterus.

Even further, in accordance with a preferred embodiment thereof, the present invention provides a catheter system for implanting embryos in a uterus, comprising: a catheter outer sleeve having a longitudinal cylindrical hollow between a sleeve distal end and a sleeve proximal end, for providing safe catheter access to a such uterus by a catheter having a catheter distal end and a catheter proximal end; such sleeve distal end comprising an outwardly convex end cap, for protecting such cylindrical hollow from accumulating mucuslike material when such catheter outer sleeve is pushed through a cervix, and an outwardly-swivelable connection between such end cap and such catheter outer sleeve, for permitting passage of a such catheter distal end from such cylindrical hollow into access to the uterus when such catheter distal end is pushed against such end cap to swivel such end cap outwardly and move such catheter distal end through such sleeve distal end.

Even additionally, this invention provides such a system further comprising: an inner catheter means, having a catheter distal end and a catheter proximal end, for transporting a such embryo through such cylindrical hollow of such outer sleeve into access to such uterus and for depositing such embryo in such uterus. And it provides such a system wherein such catheter distal end comprises: an outwardly convex second end cap for protecting such inner catheter means when such catheter distal end is pushed through such sleeve distal end; and a catheter distal opening for depositing a such embryo, such catheter distal opening comprising a side port adjacent such second end cap. It also provides such a system further comprising: locating means for locating such catheter distal end in a such uterus, such locating means comprising first stop means on such catheter outer sleeve for abutting a cervix entrance to such uterus, and second stop means settable along such inner catheter means for limiting insertion of such catheter distal end of such inner catheter means to a desired implanting location when such inner catheter means is inserted into a such uterus.

Moreover, according to a preferred embodiment of this invention, it provides a catheter system for implanting embryos in a uterus, comprising, in combination, the steps of: providing a catheter outer sleeve having a longitudinal cylindrical hollow between a sleeve proximal end and a sleeve distal end having an outwardly convex end cap and an outwardly-swivelable connection between such end cap and such catheter outer sleeve; providing a catheter having a catheter proximal end and a catheter distal end having an opening for transmission of a such embryo, such catheter being sized for moving through such longitudinal cylindrical hollow; loading at least one such embryo into such catheter distal end; placing such catheter into such sleeve proximal end of such catheter outer sleeve and moving such catheter forward until such catheter distal end is approaching such sleeve distal end; introducing such sleeve proximal end through a cervix to a desired stop location; further moving such catheter forward into such end cap of such catheter outer sleeve, outwardly swiveling such end cap, and further moving such catheter distal end forward into such uterus to a desired implanting location; and flushing such embryo out of such catheter distal end.

It even further provides such a system wherein such catheter distal end of such catheter comprises: a second end cap for protecting such catheter when such catheter distal end is pushed through such sleeve distal end; and a catheter distal opening for depositing a such embryo, such catheter distal opening comprising a side port adjacent such second end cap; and, further, wherein: such catheter outer sleeve further comprises first stop means located along such catheter outer sleeve for limiting insertion to such desired stop location when such catheter outer sleeve is introduced through the cervix; and such catheter further comprises second stop means settable along such catheter for limiting insertion to such desired implanting location when such inner catheter means is inserted into a such uterus.

Even moreover, in accordance with a preferred embodiment thereof, this invention provides, for use in a catheter system for implanting embryos in a uterus, wherein the steps in such system include providing a catheter outer sleeve having a longitudinal cylindrical hollow between a sleeve proximal end and a sleeve distal end having an outwardly convex end cap and an outwardly-swivelable connection between such end cap and such catheter outer sleeve, providing a catheter having a catheter proximal end and a catheter distal end having an opening for transmission of a such embryo, such catheter being sized for moving through such longitudinal cylindrical hollow, loading at least one such embryo into such catheter distal end, placing such catheter into such sleeve proximal end of such catheter outer sleeve and moving such catheter forward until such catheter distal end is approaching such sleeve distal end, introducing such sleeve proximal end through a cervix to a desired stop location, further moving such catheter forward into such end cap of such outer sleeve, outwardly swiveling such end cap, and further moving such catheter distal end forward into such uterus to a desired implanting location, and flushing such embryo out of such catheter distal end, a method of making such outwardly-swivelable connection between such end cap and such outer sleeve, comprising the steps of: providing an outwardly convex end portion at such sleeve distal end integral with such catheter outer sleeve; and cutting to partially sever such end portion from such catheter outer sleeve transversely just beneath such end portion around at least about 200 degrees of a circumference around such convex end portion; whereby an unsevered part of such end portion provides a hinge means comprising such outwardly-swivelable connection.

Also, this invention provides, in accordance with a preferred embodiment thereof, a catheter system for assisting implanting embryos in a uterus wherein such end opening means is a slit, normally closed but openable for permitting passage of a such inner catheter pushed along such central axis from within such cylindrical hollow into access to the uterus. It also provides such a system wherein such end opening means of such sleeve distal end is a cross-cut slit, normally closed but openable for permitting passage of a such inner catheter pushed along such central axis from within such cylindrical hollow into access to the uterus.

Even further, according to a preferred embodiment thereof, this invention provides a catheter system for assisting implanting embryos in a uterus, comprising: catheter sleeve means, having a sleeve distal end and a sleeve proximal end and having, between such sleeve distal end and such sleeve proximal end, a longitudinal cylindrical hollow having a central longitudinal axis, such catheter sleeve means being structured and arranged for containing an inner catheter in such cylindrical hollow, such catheter sleeve means comprising end cap means, disposed along an intersection of such central axis at such sleeve distal end, for substantially enclosing such cylindrical hollow at such sleeve distal end to protect such cylindrical hollow from accumulating mucuslike material when such catheter sleeve means is pushed through a cervix, such end cap means comprising end opening means, disposed along such intersection of such central axis at such sleeve distal end, for permitting passage of an inner catheter along such central axis from within such cylindrical hollow into access to the uterus; said catheter sleeve means being structured and arranged for travel of such sleeve distal end through the cervix for assistance in implanting embryos; and wherein such catheter sleeve means comprises a longitudinal wire-stiffening means for wire-stiffening of such catheter sleeve means. It also provides such a catheter system wherein such wire-stiffening means comprises substantially all of a longitudinal dimension of such catheter sleeve means; and, further, wherein such wire-stiffening means comprises a metal wire; and, further, wherein such metal wire comprises a surface of such longitudinal cylindrical hollow; and, further, wherein such wire-stiffening means is constructed and arranged to permit holding a bent shape and provide shape-maintaining support.

Moreover, according to a preferred embodiment thereof, this invention provides a catheter system for implanting embryos in a uterus, comprising: an inner catheter, having a catheter distal end and a catheter proximal end, structured and arranged to transport the embryos into access to the uterus and to deposit such embryo in the uterus; and a catheter outer sleeve having a longitudinal cylindrical hollow between a sleeve distal end and a sleeve proximal end, structured and arranged to provide safe catheter access to the uterus by such inner catheter; wherein such inner catheter comprises a proximal portion having a larger external diameter than an external diameter of a distal portion of such inner catheter. It also provides such a catheter system wherein such catheter outer sleeve comprises a proximal portion having a larger internal diameter than an internal diameter of a distal portion of such catheter outer sleeve and having a thicker wall than the wall of such distal portion of such catheter outer sleeve.

And it provides such a catheter system wherein a distal end of such distal portion of such catheter outer sleeve comprises more flexible material than a remainder of such distal portion of such catheter outer sleeve, whereby such catheter outer sleeve comprises at least three different stiffnesses along such longitudinal hollow cylinder, in increasing-stiffness order from such distal end to such proximal end of such longitudinal hollow cylinder; and, further, wherein such proximal portion of such inner catheter is at least as long as such proximal portion of such catheter outer sleeve; and, further, wherein such proximal portion of such catheter outer sleeve is at least about 10 centimeters long; and, further, wherein such distal portion of such catheter outer sleeve is at most about 5 centimeters long.

Yet moreover, according to a preferred embodiment thereof, this invention provides a catheter system for assisting implanting embryos in a uterus, comprising: a catheter outer sleeve having a sleeve distal end and a sleeve proximal end and having, between such sleeve distal end and such sleeve proximal end, a longitudinal cylindrical hollow having a central longitudinal axis, such catheter outer sleeve being structured and arranged to contain an inner catheter in such cylindrical hollow, such catheter outer sleeve comprising a longitudinal wire-stiffener structured and arranged to stiffen such catheter outer sleeve; said catheter outer sleeve being structured and arranged to permit travel of such sleeve distal end through a cervix to assist in implanting embryos; wherein such catheter outer sleeve comprises a proximal portion having a larger internal diameter than an internal diameter of a distal portion of such catheter outer sleeve; and, further, wherein such wire-stiffener comprises substantially all of a longitudinal dimension of such catheter outer sleeve. And it provides such a catheter system further comprising an inner catheter, having a catheter distal end and a catheter proximal end, structured and arranged to transport the embryos into access to the uterus and to deposit the embryos in the uterus; and, further, wherein such inner catheter comprises a proximal portion having a larger external diameter than an external diameter of a distal portion of such inner catheter; and, further, wherein such proximal portion of such inner catheter is at least as long as such proximal portion of such catheter outer sleeve. And it provides such a catheter system wherein such catheter outer sleeve comprises an end cap, disposed along an intersection of such central axis at such sleeve distal end, to substantially enclose such cylindrical hollow at such sleeve distal end to protect such cylindrical hollow from accumulating mucus-like material when such catheter outer sleeve is inserted into the uterus, such end cap comprising an end opener, disposed along such intersection of such central axis at such sleeve distal end, to permit passage of a such inner catheter along such central axis from within such cylindrical hollow into the uterus.

Yet in addition, according to a preferred embodiment thereof, this invention provides a catheter system for implanting embryos in a uterus, comprising: a catheter outer sleeve having a longitudinal cylindrical hollow between a sleeve distal end and a sleeve proximal end, structured and arranged to provide safe catheter access to the uterus by an inner catheter having a catheter distal end and a catheter proximal end; said sleeve distal end comprising an internally substantially-non-concave end cap, structured and arranged to protect such cylindrical hollow from accumulating mucuslike material when such catheter outer sleeve is pushed through a cervix, and an outwardly-swivelable connection between such end cap and such catheter outer sleeve, such sleeve distal end being structured and arranged to permit non-destructive passage of a such catheter distal end from such cylindrical hollow into access to the uterus when such catheter distal end is pushed against such internally substantially-non-concave end cap, thereby swiveling such end cap outwardly and moving such catheter distal end through such sleeve distal end.

And it provides such a catheter system wherein said outwardly-swivelable connection is a unitary part of such sleeve distal end; and, further, wherein such catheter outer sleeve comprises a long metal tube connected to a short plastic distal end comprising such swivelable end cap; and, further, wherein such outwardly-swivelable connection is a unitary part of such sleeve distal end, and such end cap is a unitary part of such sleeve distal end. It further provides such a catheter system wherein an internal surface of such internally substantially-non-concave end cap lies substantially within a single flat plane; and, further, wherein said internally substantially-non-concave end cap is outwardly convex. Also, this invention provides such a catheter system wherein such sleeve distal end further comprises mucus-trapping means for trapping nearby mucus during a such passage of a such catheter distal end from such cylindrical hollow into access to the uterus; and, further, wherein such mucus-trapping means comprises roughened surface portions to assist in such.trapping of mucus. And it provides such a catheter system wherein such roughened surface portions comprise both external and internal surfaces of such sleeve distal end; and, further, wherein such end cap comprises an outwardly convex flexible end on such catheter outer sleeve and such outwardly-swivelable connection comprises a partial planar cut separating, except for a remaining transverse hinge portion, such outwardly convex flexible end from such catheter outer sleeve, whereby such end cap comprises a planar internal surface; and, further, wherein said partial planar cut comprises an angle between such planar internal surface and a transverse plane perpendicular to a longitudinal axis of such longitudinal hollow of from about 0 degrees to about 45 degrees; and, further, wherein said angle is from about fifteen degrees to about twenty degrees.

Even in addition, according to a preferred embodiment thereof, this invention provides a catheter system for single-person implanting of an embryo in a uterus, comprising, in combination, the steps of: providing a wire-stiffened catheter outer sleeve having a longitudinal cylindrical hollow between a sleeve proximal end and a sleeve distal end, wherein a proximal portion of such cylindrical hollow has a larger internal diameter than an internal diameter of a distal portion of such cylindrical hollow; providing an inner catheter having a catheter proximal end and a catheter distal end having an opening for transmission of a such embryo, such catheter being sized for moving through such longitudinal cylindrical hollow, wherein a proximal portion of such inner catheter has a greater catheter wall thickness than a distal portion of such inner catheter, and wherein such proximal portion of such inner catheter has a larger external diameter than an external diameter of such distal portion of such inner catheter, and said inner catheter being structured and arranged to supportingly fit within such outer sleeve, thereby providing substantially greater catheter system stiffness; affixing a syringe at such proximal end of such inner catheter; loading such embryo into such inner catheter distal end; placing such inner catheter into such proximal end of such outer sleeve and moving such inner catheter forward until such inner catheter distal end is approaching such sleeve distal end; introducing such sleeve proximal end into a cervix to a desired stop location; further moving such inner catheter forward into such end cap of such outer sleeve, outwardly swiveling such end cap, and further moving such catheter distal end forward into access to the uterus to a desired implanting location; and flushing such embryo out of such catheter distal end.

It also provides such a catheter system wherein, during such step of further moving such inner catheter forward, forward travel of such inner catheter is limited by a distal end of such proximal portion of such inner catheter being blocked when reaching a distal end of such proximal portion of such outer sleeve, thereby assisting in avoiding injury to the uterus from too much forward travel of such inner catheter; and, further, wherein such step of moving such inner catheter forward may be accomplished by one hand of a catheter system user because of such substantially greater catheter system stiffness.

And it also provides a described catheter system wherein such inner catheter means further comprises, located adjacent such proximal end of such inner catheter means, indicator means for indicating a direction of opening of such side port. It also provides a described catheter system wherein such catheter outer sleeve further comprises a bend in such distal portion of such catheter outer sleeve to better assist in pushing through the cervix; and, further, wherein such catheter outer sleeve further comprises, located adjacent such proximal end of such catheter outer sleeve, indicator means for indicating a direction of such bend of such distal portion of such catheter outer sleeve. And it also provides a described catheter system wherein such swivel means is constructed and arranged in such manner that such end cap means swivels back to a closed position when such catheter sleeve means is pulled from the cervix.

BRIEF DESCRIPTION OF THE DRAWINGS

FIG. 1 is a partial sectional elevation view illustrating a preferred embodiment of a catheter system for implanting embryos, according to the present invention, shown inserted into a woman's uterus.

FIG. 2 is an exploded elevation view of the catheter system.

FIG. 3 is an enlarged, fragmented elevation view, in cross section, of a preferred embodiment of the outer sleeve of the catheter system.

FIG. 4 is a enlarged elevation view of the introducing-implanting end of the outer sleeve.

FIG. 5 is a cross-section plan view of the outer sleeve through section 5—5 of FIG. 4.

FIG. 6 is an enlarged perspective view of the outer sleeve end, shown in its open position.

FIG. 7 is an enlarged cross-sectional elevation view of the implanting end of the inner catheter.

FIG. 8 is an enlarged elevation view of the implanting end of the inner catheter.

FIG. 9 is a cross-section plan view of the inner catheter through section 9—9 of FIG. 8.

FIG. 10 is an enlarged cross-section partial elevation view showing the inner catheter within the outer sleeve at its implanting end.

FIG. 11 is a perspective view showing a second embodiment of the implanting end of the inner catheter.

FIG. 12 is a perspective view showing a third embodiment of the implanting end of the inner catheter.

FIGS. 13 through 19 illustrate a preferred embodiment of the method of use of the catheter system of the present invention.

FIG. 23 is a top view illustrating an additional preferred embodiment of the catheter system of the present invention.

FIG. 24 is a cross-sectional view of the additional preferred embodiment, taken through the center lines looking downward, illustrating in detail the preferred construction and the outer sleeve as it relates to the inner catheter.

FIG. 25 is a perspective view of the winged locking mechanism for connecting a syringe to the catheter system.

FIG. 26 is an enlarged view, partially in section, of a preferred embodiment of the end cap of the outer sleeve and the implanting end of the inner catheter.

FIG. 27 is an enlarged cross-sectional view of the outer sleeve containing the inner catheter taken through section 27—27 of FIG. 23.

DETAILED DESCRIPTION OF A PREFERRED EMBODIMENT AND THE BEST MODE OF PRACTICE

Figure 20:
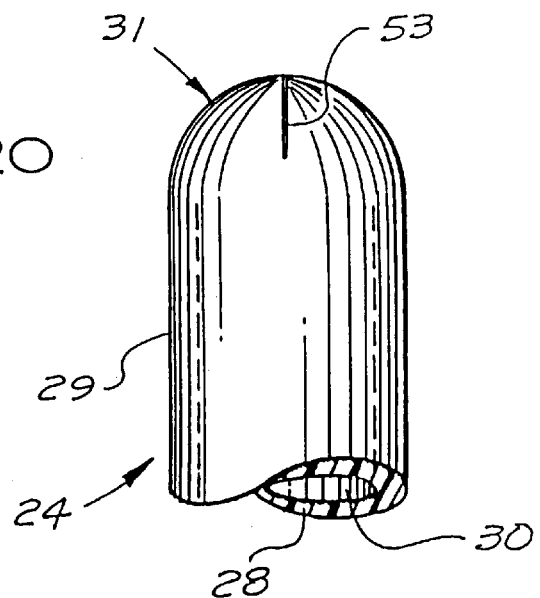
FIG. 20 is a enlarged elevation view of the introducing-implanting end of the outer sleeve illustrating alternate, but less preferred, embodiments of the end opening means.

Shown in FIG.1 is a preferred embodiment of the catheter system 20 of the present invention, shown inserted into the uterus 21 of a woman for the purpose of depositing embryos 22. The catheter system 20 is comprised of catheter sleeve means embodied by catheter outer sleeve 24 and inner catheter means embodied by an inner catheter 25. The outer sleeve 24 contains and protects the inner catheter 25 (the two being concentrically disposed), and the embryos 22 within, while the catheter system 20 is inserted into the vagina, through the cervix 26, and into the uterus 21. Then there is performed embryo depositing and placement at a predetermined depth (from the exterior of the cervix) D1 within the uterus 21. Once deposited within the uterus 21, the embryos 22 will normally eventually attach to the uterus wall 27.

The outer sleeve 24 is substantially tubular, as shown, and has a longitudinal round-cylindrical hollow 28 (having interior surface 30) appropriately sized for loosely containing the inner catheter 25 and extending the full length of the outer sleeve 24 (i.e., from its distal or depositing end 31 to its proximal or manipulating end 40). Integral with the outer sleeve 24, and at its depositing end 31, is end cap means preferably embodied by a swivelable cap 32 which remains in a closed position 33 (see FIGS. 3, 4, and 10), closing, streamlining, and protecting the depositing end 31, and blocking the cylindrical hollow 28, until being pushed forwardly to an open position 34 by the extending movement of the inner catheter 25. The swivelable cap 32, while remaining in a closed position 33, protects the interior of the outer sleeve 24 at the depositing end 31 from accumulating deposits of mucus 35 when the outer sleeve 24 is inserted through the cervix 26.

The outer sleeve 24 incorporates a stop means embodied by a flange 36 extending outwardly perpendicular from the outer sleeve 24 and of a diameter suitable for providing a limiting stop 37 at the entrance 38 of the cervix 26, and thus controlling the depth D2 that the outer sleeve 24 can be inserted into the cervix 26. This depth D2 is greater than the distance required to pass through the cervix 26, but less than the depth desired for depositing the embryos 22. This portion of the outer sleeve 24 (which is inserted through the cervix 26 to depth D2), extending from flange 36 to the swivelable cap 32, is the insertable portion 29 which is relatively small in outside diameter and flexible enough for conforming to the shape of the cervical passage.

Extending from flange 36 toward the manipulating (proximal) end 40, the outer sleeve 24 incorporates an increased outer diameter 41 for added rigidity in controlling the insertion of the catheter system 20 of the preferred embodiment of the present invention into the cervix 26. Also incorporated as a feature of the increased outer diameter 41 portion, located near the manipulating end 40, is handle means 42 for convenience of grasping the outer sleeve 24. Located at the manipulating end 40 of the outer sleeve 24 is a second flange 43 useful (as will be described) for controlling the movement of the inner catheter 25 in providing the desired implanting depth D1.

Alternately, it is noted that, as another preferred embodiment in which the sleeve may be bendable to conform to the shape of the cervix rather than flexible as stated above, outer sleeve 24 may be made of, for example, a thin-walled stainless steel tube (preferably about 2 mm in outside diameter with a wall thickness of about 0.2 mm). Then insertable portion 29 may be bent to a specific cervical shape. In this embodiment, the distal end (about the last 1 cm thereof) of sleeve 24 is still made of a soft plastic to permit making an end cap as shown in this specification (preferably with about a 3 mm nominal outer diameter and with an internal diameter fitting tightly over the distal end of the stainless steel tube to provide integrity. This alternative embodiment (embodying herein such catheter system wherein such catheter outer sleeve comprises a long metal tube connected to a short plastic distal end comprising such swivelable end cap), while possibly not economically optimal, also provides additional stiffness and support to the catheter system, which is important; and such support will be discussed further with respect to the embodiment of FIG. 23 et seq.

With respect to the drawings, again, he inner catheter 25 is a hollow, flexible, very-small-diameter longitudinal tube, sized to fit, and be free to slide concentrically within, the longitudinal cylindrical hollow 28 of the outer sleeve 24 along its axis or centerline CL (see FIG. 3.). At the depositing (distal) end 39, the inner catheter 25 preferably incorporates an integral domed end cap 44 with a side port 45 interconnecting to the round-cylindrical interior passage 57 of the inner catheter 25. At the manipulating (proximal) end 46 of the inner catheter 25 is a receiver 47 into which a syringe 48 may be inserted. In use, the distal or depositing end 39 of the inner catheter 25 is loaded with buffer solution and embryos, then inserted into the manipulating end 40 of the outer sleeve 24 far enough so that the depositing end 39 approaches but does not contact the swivelable cap 32 (in its normal closed position); thus the depositing end 39 of the inner catheter 25 is not yet protruding from the depositing end 31 of the outer sleeve 24. Based upon prior soundings of the depth of the uterus, the desired depth D1 at which the embryos are to be deposited is determined. The amount this depth D1 is greater than the distance D2 (that the insertable portion 29 of the outer sleeve 24 inserts into the cervix 26) determines the distance D3 that the inner catheter 25 will be required to extend beyond the end of the outer sleeve 24 for implanting. When this distance D3 is established and added to distance that the inner catheter 25 is short of exiting from the outer sleeve 24, a snug-fitting second stop means embodied by movable stop 50 is positioned on the inner catheter 25 a corresponding distance away from the second flange 43 of the outer sleeve 24.

The catheter system 20 is then inserted into the uterus 21 through the cervix 26. Any mucus 35 that the insertable portion 29 of the outer sleeve 24 encounters and picks up remains on its exterior. After the described preferred insertion of the insertable portion 29 of the outer sleeve 24 into the uterus, the inner catheter 25, held concentrically by the outer sleeve 24, is pushed forward along the axis or longitudinal centerline CL of the outer sleeve 24 the distance available until the movable stop 50 contacts the outer sleeve's second flange 43. This forward concentric movement of the inner catheter 25 pushes its domed end cap 44 against the outer sleeve's swivelable cap 32 (situate also along the centerline CL of the outer sleeve 24), opening it, and allowing the inner catheter 25 to extend beyond the outer sleeve 24 to the depth D1. Any mucus 35 encountered and picked up by the outer sleeve 24 (especially at its swivelable cap 32) is pushed aside by the opening movement of the swivelable cap 32. Thus the inner catheter 25 in exiting from the interior of the outer sleeve 24 remains free of mucus 35. With the embryos 22, which are to be implanted, contained inside near the side port 45 at the depositing end 39 of the inner catheter 25, and the inner catheter 25 shielded from passing through an accumulation of mucus 35, the depositing of embryos 22 is not hindered by mucus 35. This arrangement embodies in this invention an end cap means, disposed along an intersection of such central axis at such sleeve distal end, for substantially enclosing such cylindrical hollow at such sleeve distal end to protect such cylindrical hollow from accumulating mucuslike material when such catheter sleeve means is inserted into a such uterus, such end cap means comprising end opening means, disposed along such intersection of such central axis at such sleeve distal end, for permitting passage of an inner catheter along such central axis from within such cylindrical hollow into a such uterus. Once the inner catheter 25 is positioned at depth D1, the embryos 22, in their buffer solution, are hydraulically flushed from the side port 45 by means of the syringe 48 (and the flow of liquid through the interior passage 57 in well-known ways). After the embryos 22 are deposited within the uterus 21, the catheter system 20 is withdrawn from the cervix 26, uterus 21 and the vagina.

FIG. 2 illustrates the relative proportions of the components of the catheter system 20, shown un-assembled, and composed of the outer sleeve 24, inner catheter 25 and the movable stop 50. Additionally illustrated in enlarged shortened cross section in FIG. 3 is the outer sleeve 24. Its features include the insertable portion 29 extending from the depositing end 31, with the swivelable cap 32 located centrally at the axis or centerline CL, to the flange 36 whose upper surface is the limiting stop 37 to restrict further insertion into the cervix 26. Extending from the flange 36 to the manipulating end 40, the outer sleeve 24 is of increased outer diameter 41. At the manipulating end 40 is a second flange 43 for providing a gauging surface with which the movable stop 50 may make contact. The longitudinal round-cylindrical hollow 28 extends from depositing end 31 to manipulating end 40 along axis or centerline CL. Additionally located near the manipulating end 40 is a handle means 42 which is sized and shaped for convenient handling of the outer sleeve 24. The movable stop 50 is made of silicone and has an inside diameter that is sized for a snug fit over the outside diameter of the concentrically-located inner catheter 25. The fit allows the movable stop 50 to be positioned as required on the inner catheter 25, yet remain in that position during use. The inner catheter 25 has a depositing end 39 and at the opposite (proximal) end, a receiver 47 with an appropriately-sized internal socket for the snug-fitting attachment of a syringe. The proportional lengths of the outer sleeve 24 and the inner catheter 25 are such that a first person can insert and position the outer sleeve 24 within the patient and advance the inner catheter 25 while a second person can, from a convenient distance, handle the syringe 48 and perform the flushing of the embryos into the uterus.

In further description of the outer sleeve 24, in addition to FIG. 3, the depositing end 31 is shown in elevation view in FIG. 4, in cross-section in FIG. 5 and in perspective in FIG. 6. The material from which the entire outer sleeve 24 is constructed could preferably be siliconized polyvinylchloride, plastisol polyvinyl, or polyethylene. Alternately, either the entire insertable portion 29, or the end 0.5–1.0 centimeter of the depositing end 31 of the insertable portion 29 could be made of such just-mentioned material whereas the remainder of the outer sleeve 24 could be constructed of borosilicate or, as mentioned earlier, of a metal tubing like stainless steel. The insertable portion 29 preferably is about 1.8–2.0 millimeters in outside diameter with a length of about 3.5 centimeters. The increased outer diameter 41 portion is preferably about 4.0 millimeters in outside diameter. Extending concentrically the length of the outer sleeve 24, excepting the swivelable cap 32 at the depositing end 31, the interior diameter 30 of the cylindrical hollow 28 is preferably about 1.5 millimeters. In manufacture, the depositing end 31 could be initially completely blocked with an integral outwardly convex end (preferably hemispherical), then a very thin transverse cut 55 (see FIG. 4), preferably by blade, but which may also be made by laser, would be made, nearly severing the hemisphere (preferably about 300 degrees of the circumference around the convex end, depending upon the material and geometry of the sleeve end, and preferably at least about 200 degrees of the circumference so that the hinge-action may operate properly), with the remaining un-severed portion forming the hinge 56. The cut 55, by blade, would extend roughly perpendicular to (no more slanted than about 45 degrees in the direction of swivel) and fully through the longitudinal cylindrical hollow 28 with the uncut amount being the hinge 56 as shown in cross-section in FIG. 5. Then the hemisphere, i.e. the swivelable cap 32, remaining intact and partially attached to the depositing end 31 of the insertable portion 29, in the closed position 33, blocks the interior of cylindrical hollow 28 until being forcibly moved to an open position 34 as shown in FIG. 6 (by the movement along the axis or centerline CL of the inner catheter 25).

Figure 21:
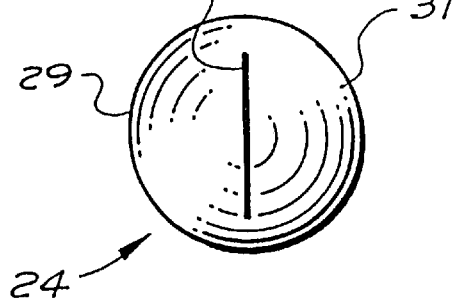
FIG. 21 is a top view of the embodiments of FIG. 20 illustrating a first alternate embodiment of the end opening means.
Figure 22:
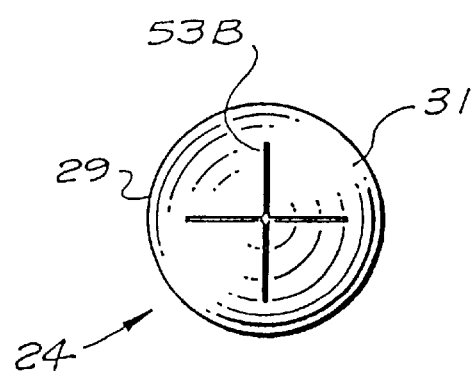
FIG. 22 is a top view of the embodiments of FIG. 20 illustrating a second alternate embodiment of the end opening means.

Although the preferred configuration of the depositing end 31 of the outer sleeve 24 has been fully described, alternate (but less preferred) configurations can be used herein. For example, illustrated in FIG. 20 (in a view similar to that of FIG. 4 but without the transverse cut 55) is the outer sleeve 24 comprising an insertable portion 29 having an approximately hemispherical depositing end 31. Specifically illustrated in FIG. 20 is the first alternate embodiment of the end opening means embodied by a single cut or slit 53 (53A in FIG. 21) on the hemispherical depositing end 31 of outer sleeve 24. FIG. 21 is a top view illustrating the cut or slit 53A. This embodies herein a system wherein such end opening means is a slit, normally closed but openable for permitting passage of a such inner catheter pushed along such central axis from within such cylindrical hollow into a such uterus. FIG. 22 is an alternate top view of FIG. 20 illustrating a second alternate embodiment of the end opening means which is embodied by a cross-cut slit 53B on the hemispherical depositing end 31 of outer sleeve 24. The single slit 53A and the cross-cut slit 53B in, respectively, the first and second alternate embodiments of the end opening means are normally closed to maintain a closed depositing end 31 along the axis or centerline CL but are openable when and if catheter distal end 39 is pushed through said sleeve distal end 31 (occurring also along axis or centerline CL). The second alternate embodiment embodies herein such a system wherein such end opening means of such sleeve distal end is a cross-cut slit, normally closed but openable for permitting passage of a such inner catheter pushed along such central axis from within such cylindrical hollow into a such uterus.

The inner catheter 25, is a lengthy (preferably about 70 centimeters in overall length) flexible tube preferably constructed in one piece of Teflon or polyethylene with about a 0.5 millimeter inside diameter and about a 1.2 millimeter outside diameter (with the exception, of course, of the described special features at both ends). At the manipulating end 46 is the receiver 47 for accepting a syringe 48 (see FIG. 1). At the depositing end 39 is a second end cap means embodied by a domed end cap 44 (roughly hemispherical for fending off mucus and pushing smoothly on swivelable cap 32) and also catheter distal opening means embodied by side opening or port 45 for discharging the embryos to be deposited. With the depositing end 39 of the inner catheter 25 shown in longitudinal cross-section in FIG.7, the round domed end cap 44 is shown blocking the straight through flow path of the interior passage 57. Located through the side wall, directly under the domed end cap 44, is the side port 45, which is preferably a round opening which intersects with, and completes the interior passage 57 allowing a side discharge path. At the location on the inner catheter 25 opposite to where the side port 45 intersects the interior, structural strength is compromised, and as a preventative against breakage, strengthening means embodied by the strengthened intersection 58, radiused with additional material, is provided. In addition to adding strength, the intersection 58, being radiused, also provides for a smoother, more streamlined flow path. This helps in cleaning, loading and flushing the inner catheter 25.

In FIG. 8, the inner catheter 25 is shown rotated approximately 45 degrees with the side port 45 shown completing the flow path of the interior passage 57. Also shown are indicia means embodied by indicia or markings 60, which are evenly spaced and continue the full length on the exterior of the inner catheter 25. These markings 60 may be graduated divisions referring to the volume of the interior passage 57 beginning at the side port 45. Their use is described, for example, in FIGS. 14A–14C. Indicia means for indicating longitudinal distance to assist in attaining a desired implanting location, embodied by similar additional graduated markings 60 (see FIG. 13) referring to length may be included to establish the location at which the movable stop 50 is positioned to provide a given extension dimension of the inner catheter 25 from the end of the outer sleeve 24. A cross-section through the inner catheter 25 at the side port 45 location is shown in FIG. 9. The additional wall thickness derived from the radiused intersection 58 is shown in location opposite the side port 45.

FIG. 10 illustrates in cross-section the depositing ends 31 of the outer sleeve 24, and within its cylindrical hollow 28, the inner catheter 25, both positioned approximately as they would be while being inserted into the desired uterus position. With the swivelable cap 32 in its normally closed position 33, the inner catheter 25 is protected from any accumulation of mucus. When the inner catheter 25 is extended from the outer sleeve 24, the domed end cap 44 contacts the underside of the swivelable cap 32 of the outer sleeve 24, pushing it to the open position 34 (shown by dotted lines) as the hinge 56 flexes. As the inner catheter 25 extends out of the outer sleeve 24, any remaining mucus which may be encountered is pushed aside or collected on the domed end cap 44 and not forced into the side port 45.

Although the preferred shape of the depositing end 39 of the inner catheter 25 has been fully described, alternate methods of construction are illustrated in FIGS. 11 & 12 with the interior passage 57 continuing straight and unobstructed, without the domed end cap, and exiting the end of the inner catheter 25. FIG. 11 incorporates side wall relief or opening means embodied by two reliefs 61, spaced at 180 degrees apart, at the end of the inner catheter 25. Thus, for example, even in the event of the depositing end 39 of the inner catheter 25 butting firmly against a wall of the uterus, the embryos may be discharged from the inner catheter 25 through the reliefs 61. In the most simplified form, the inner catheter 25 of FIG. 12 incorporates a blunt end opening 62. Although the benefits from the features of the previously described inner catheters are not available with a blunt opening 62, the combined use with the outer sleeve 24, as herein taught, offers protection from mucus while within the outer sleeve 24.

FIGS. 13 through 19 describe pictorially the steps involved in the use of the catheter system 20. With reference to FIG. 13, prior to the use of the catheter system 20, a sounding is performed to determine the depth of the uterus 21 and the distance D1 from the entrance 38 of the cervix 26 to the location within the uterus 21 where the embryos 22 are to be deposited for implanting. The depositing end 39 of the inner catheter 25 is inserted into the interior of the outer sleeve 24 at the manipulating end 40 and the movable stop 50 is adjusted to the proper position as shown in FIG. 13. "S" represents the depth of the uterus 21 as determined by the sounding. The desired depth at which the embryos are to be deposited is shown as D1. D2 is the distance that the insertable portion 29 of the outer sleeve 24 will insert into the cervix 26. D3 is the distance that the inner catheter 25 will be required to extend beyond the end of the outer sleeve 24 for implanting at the desired depth D1. D4 is the distance that the inner catheter 25 will be short of exiting from within the outer sleeve 24 when the implanting process is begun. The sum of distances D3 and D4 is E1, the extending distance, the amount the inner catheter 25 will extend for implanting. The extending distance E1 is equal to E2, the measurement at which the snug fitting movable stop 50 is to be positioned, the distance short of contacting the second flange 43 at the manipulating end 40 of the outer sleeve 24. As discussed with FIG. 8, markings 60 may be incorporated on inner sleeve 25 to provide dimensional aid in locating movable stop 50 at distance E2 from second flange 43.

After adjustment is completed, the inner catheter 25 (with the movable stop 50 being unmoved and remaining in place) is withdrawn from the outer sleeve 24. The interior of the inner catheter 25 is rinsed with a buffer solution by a tuberculin syringe (in a well known manner) and then loaded as illustrated in FIGS. 14A, 14B, and 14C and according to the following instructions. As shown in FIG. 14A, with a syringe 48 inserted into the receiver 47 at the manipulating end 46 of the inner catheter 25, draw buffer solution 63 into the side port 45 at the depositing end 39 to the marking 60 corresponding to about 0.2 milliliters. Draw in a small amount of air, then load embryos 22 into side port 45 as in FIG. 14B. Draw in another small amount of air, then draw up about 0.005 milliliters of buffer solution 63. FIG. 14C shows inner catheter 25 appropriately loaded with buffer solution 63, two air spaces 64 and embryos 22, with markings 60 used to determine quantities.

Then, as shown in FIG. 15A, insert the inner catheter 25 into cylindrical hollow 28 at the manipulating end 40 of the outer sleeve 24 until the depositing end 39 of the inner catheter 25 is just short of contacting the swivelable cap 32 (or the less preferred alternate slits 53) of the outer sleeve 24 (as shown in FIG. 15B). In this position, the swivelable cap 32 remains in the closed position 33. Then, with the catheter system 20 now prepared for usage, insert the depositing end 31 of the insertable portion 29 of the outer sleeve 24 into the cervix 26 of the patient, as shown in FIG. 16A. Then (see FIG. 16B) insert the outer sleeve 24 through the cervix 26, until its limiting stop 37 of flange 36 contacts the cervix entrance 38.

Then, after the outer sleeve 24 is in position, advance the inner catheter 25 until the movable stop 50 contacts the second flange 43 of the outer sleeve 24. During this process, as shown in FIG. 17, the inner catheter 25 pushes aside the swivelable cap 32 (or through the less preferred slits 53) of the outer sleeve 24 to the open position 34. When advancement is completed, the depositing end 39 of the inner catheter 25 is properly positioned in the uterus 21 for implanting. Next, as shown in FIG. 18, using syringe 48 inserted into the receiver 47 of the inner catheter 25, slowly inject about 0.02 to 0.03 milliliters of the contents of the inner catheter 25 into the uterus 21. This injection transfers a small amount of buffer solution 63 along with the embryos 22 from the side port 45 into a desired location within the uterus 21 where the embryos 22 may attach the uterus wall 27. Then, after such implanting, the catheter system 20 is to remain unmoved for about one minute. Then, carefully withdraw the outer sleeve 24 and inner catheter 25 from the patient, and, as shown in FIG. 19, with a microscope 66, insure that embryos do not remain in the inner catheter 25.

FIG. 23 illustrates another preferred embodiment 70 of the present invention. This preferred embodiment 70 of the present invention operates in essentially the same manner and for the same purpose as has been described above, but with the differences as below described. Preferred embodiment 70 of the catheter system of the present invention includes an outer sleeve 68 and an inner catheter 69. In FIG. 23, the distal end 71 of the inner catheter 69 protrudes from the distal end 72 of the outer sleeve 68 through the open end cap 73 of the outer sleeve 68.

The outer sleeve 68 is a long cylindrical tube with a preferred length of approximately 15 centimeters (cm), which sleeve 68 contains the inner catheter 69, the two being concentrically arranged. Outer sleeve 68 includes distal end 72, end cap 73, distal portion 75, proximal portion 76, and winged flange 77. The smaller-outer-diameter distal portion 75 of the outer sleeve 68 is connected to the larger-outer-diameter proximal portion 76 of the outer sleeve by a diameter-step 90 characterized by a preferred gradual change at preferably about 45 degrees (as shown, see FIG. 24). This gradual diameter-step 90 allows the distal portion 75 with a smaller outer diameter OD6 to gradually change into the proximal portion 76 with a larger outer diameter OD7. This gradual diameter-step 90 eliminates a sudden change in outer diameter which might otherwise be the site of a weak point which could bend or break easily.

The distal end 72 of the outer sleeve 68 (when end cap 73 is closed) is outwardly rounded and functions as a probe to find the pathway through the cervical canal before the end cap 73 of the outer sleeve 68 is opened. The distal end 72 of the outer sleeve 68, preferably about 5 the last millimeters (mm), may be made about a millimeter larger in diameter (preferably gradually rounded on both ends of the 5-millimeter-long bulge) than the rest of distal portion 75 to allow the physician to feel when the distal end 72 has passed through the cervix.

The end cap 73 of the outer sleeve 68 is shown in an expanded sectional view in FIG. 26. The end cap 73 of the outer sleeve 68 is preferably formed by making a cut 74 in the most distal 1.0 to 1.5 millimeters of the distal end 72 of the outer sleeve 68. This cut 74 is preferably made through the point of the distal end 72 of the outer sleeve where the sleeve solid changes from solid to hollow, as shown. By making the cut 74 here, the inner surface 81 of the end cap 73 of the outer sleeve 68 is made flat and planar, without a chamber or hollow. This solid surface makes the end cap 73 of the outer sleeve 68 easier to open when pushed against by the distal end 71 of the inner catheter 69. That is, the distal end 71 of the inner catheter 69 does not catch or snag in a depression on the inner surface 81 of the end cap 73 of the outer sleeve 68 when it is pushed against the inner surface 81 of the end cap 73. It is thus highly preferred that the inside of the end cap 73 of the present invention (including the embodiment of FIG. 3) be substantially non-concave (embodying herein that an internal surface of such internally substantially-non-concave end cap lies substantially within a single flat plane). This end cap embodies herein end cap means, disposed along an intersection of such central axis at such sleeve distal end, for substantially enclosing such cylindrical hollow at such sleeve distal end to protect such cylindrical hollow from accumulating mucuslike material when such catheter sleeve means is pushed through a cervix, such end cap means comprising end opening means, disposed along such intersection of such central axis at such sleeve distal end, for permitting passage of an inner catheter along such central axis from within such cylindrical hollow into access to the uterus.

The cut angle 82 of the end cap 73 is preferred to be between 0 and 45 degrees and is highly preferred to be between 15 and 20 degrees. This preferred range of cut angle 82 of the end cap 73 is important in this preferred embodiment for several reasons. A small angle assists in the ease of swivelability when the inner catheter 69 pushes on end cap 73. Also, if the outer sleeve 68 encounters resistance from the top, as it passes through the cervix 26 (see, e.g., FIG. 1), the end cap 73 of the outer sleeve 68 will be pushed tighter in the closed position instead of possibly sliding and breaking. In addition, with the preferred low cut angle 82 of the end cap 73, when the inner catheter 69 is withdrawn from the outer sleeve 68, the end cap 73 will close more readily (embodying herein wherein such swivel means is constructed and arranged in such manner that such end cap means swivels back to a closed position when such catheter sleeve means is pulled from the cervix). In addition, with a low cut angle 82 of the end cap 73, the end cap 73 will not be easily twisted when the further preferred embodiment 70 passes through the cervix 26. With a higher cut angle 82 of the end cap 73, the end cap 73 may become twisted when it encounters resistance through the cervix 26, which might injure the cervical mucosa. Also, if the end cap 73 becomes twisted or displaced because of a very tight cervical canal, this low cut angle 82 of the end cap 73 will lower the risk of injuring the cervix 26. (see FIG. 1 for relationship of this further preferred embodiment 70 within the cervix 26 and uterus 21). It is again noted that if the end cap is torn off and lodges in the cervix, that would be an intolerable medical result, so the cut angle problems mentioned are significant. End cap 73 and its hinge embody herein an outwardly-swivelable connection between such end cap and such catheter outer sleeve, such sleeve distal end being structured and arranged to permit non-destructive passage of a such catheter distal end from such cylindrical hollow into access to the uterus when such catheter distal end is pushed against such internally substantially-non-concave end cap, thereby swiveling such end cap outwardly and moving such catheter distal end through such sleeve distal end.

In this preferred embodiment 70, the distal portion 75 of the outer sleeve 68 is preferably approximately 4 centimeters in length, and preferably no more than 5 cm in length. The length of the distal portion 75 of the outer sleeve 68 provides a marker for the depth of insertion into the cervix 26, as 3.5 to 4.0 centimeters is an average measurement for the depth of the cervix 26 (see FIG. 1, D2). In this preferred embodiment 70, the inner diameter of the distal portion 75 of the outer sleeve 68 is preferably approximately 1.6 mm in diameter and the outer diameter OD6 of the distal portion 75 of the outer sleeve 68 is preferably approximately 2.5 mm in diameter.

In this preferred embodiment 70, the proximal portion 76 of the outer sleeve 68 is preferably approximately 11 to 12 cm in length and such proximal portion of such catheter outer sleeve is preferably at least about 10 centimeters long. The outer diameter OD7 of the proximal portion 76 of the outer sleeve 68 is preferably approximately 3.5 to 3.8 mm in diameter. The inner diameter ID7 of the proximal portion 76 of the outer sleeve 68 is preferably approximately 2.8 to 3.0 mm in diameter. Because of its larger outer diameter OD7 and inner diameter ID7 and thicker wall, the proximal portion 76 of the outer sleeve 68 is thicker and stiffer than the distal portion 75 of the outer sleeve 68 (this arrangement embodying herein outer sleeve comprising a proximal portion having a larger internal diameter than an internal diameter of a distal portion of such catheter outer sleeve and having a thicker wall than the wall of such distal portion of such catheter outer sleeve). Added stiffness helps make it easier for a physician to insert the outer sleeve 68 through the cervix 26 (See FIG. 1).

FIG. 27 illustrates a cross-sectional view, at section 27—27 of FIG. 23. Among other things, FIG. 27 illustrates longitudinal wire 93 embedded in the inner surface 94 of the outer sleeve 68 and extending slightly, as shown, into the hollow cylindrical tube of the outer sleeve 68. The preferably continuous longitudinal wire 93 is preferably embedded in the inner surface 94 of the outer sleeve 68 in the manner shown (embodying herein wherein such metal wire comprises a surface of such longitudinal cylindrical hollow) from the winged flange 77 at proximal end 78 of through the gradual diameter-step 90 to approximately a location 79 preferably about 5 mm from the distal end 72 of the outer sleeve 68 (embodying herein wire-stiffening means comprising substantially all of a longitudinal dimension of such catheter sleeve means). This wire 95 increases the stiffness of the proximal portion 76 of the outer sleeve 68, strengthens the gradual change 90, increases the stiffness of the distal portion 75 of the outer sleeve 68 and allows the distal portion 75 of the outer sleeve 68 to bend and hold a shape to "remember" a specific shape to fit an individual cervical anatomy. Preferably, the metal wire 93 is about 0.2 mm in diameter and made of 304 SS wire. This outer sleeve arrangement embodies herein such catheter sleeve means being structured and arranged for travel of such sleeve distal end through the cervix for assistance in implanting embryos, and wherein such catheter sleeve means comprises a longitudinal wire-stiffening means for wire-stiffening of such catheter sleeve means.

With special reference to FIG. 24, in this preferred embodiment 70, the outer sleeve 68 is preferably an integral, unitary piece made from the same plastics family but with three different softnesses/stiffnesses as below described. The proximal portion 76 is preferably the stiffest, least soft, portion because of its increased inner diameter ID7 and outer diameter OD7 and wall thickness and because of the wire 93 embedded in its inner surface 94 (preferably made of a 65D durometer resin, preferably DOW [TM] polyurethane 2363/65D). It is noted that the outer diameter of this proximal portion may be further increased and stiffened by mounting thereon an additional tube/sleeve of selected stiff material. The distal portion 75 of the outer sleeve 68 is preferably softer and less stiff because of its smaller inner diameter and outer diameter (and thinner wall) but is also reinforced by the wire 93 embedded in its inner surface 94 which wire 93 also allows the distal portion 75 of the outer sleeve to "remember" a specific shape (also preferably made of a 65D durometer resin, preferably DOW [TM] polyurethane 2363/65D). The distal end 72 of the outer sleeve is preferably softest and least stiff because the wire does not extend all the way to the distal end 72. Also, the preferred material is softer and more flexible and permits the hinge 84 to work properly when end cap 73 is cut as described (no more than about a cm at the distal end 72 is preferably made of DOW [TM] polyurethane 2363 [medical grade] 80A). This arrangement embodies herein wherein a distal end of such distal portion of such catheter outer sleeve comprises more flexible material than a remainder of such distal portion of such catheter outer sleeve, whereby such catheter outer sleeve comprises at least three different stiffnesses along such longitudinal hollow cylinder, in increasing-stiffness order from such distal end to such proximal end of such longitudinal hollow cylinder.

The proximal end 78 of the outer sleeve 68 is preferably attached to winged flange 77 as illustrated in FIG. 25. The winged flange 77 helps the physician hold the preferred embodiment 70. The winged flange 77 is also preferably marked with an indicator 100 (embodying herein an "indicator means") to help the physician mark the direction of the above-mentioned bend (as, for example, illustrated in FIG. 23) in the outer sleeve 68.

FIG. 26 illustrates preferable "roughened" areas 83 (for the purpose of mucus-trapping) located on the exterior surface 99 of the distal portion 75 of the outer sleeve 68. These roughened areas 83 may preferably contain hair-like protrusions, as shown, or may consist of other surface-roughening in the material of distal portion 75 of the outer sleeve 68. These roughened areas 83 act to keep mucus from attaching to the distal end 71 of the inner catheter 69 when the end cap 73 is opened by capturing the end-cap-area mucus, thus helping keep mucus away from the emerging inner catheter (embodying herein mucus-trapping means for trapping nearby mucus during a such passage of a such catheter distal end from such cylindrical hollow into access to the uterus). FIG. 26 also illustrates preferable roughened areas 89 located on the interior surface 85 of the distal end 72 of the outer sleeve 68. These roughened areas 89 also, similarly, help to keep and hold trapped any mucus entering (e.g., by capillary action when the end cap opens) into the interior of the distal end 72 of the outer sleeve 68 (when the end cap 73 is opened) rather than clinging to the inner catheter 69.

The inner catheter 69 is preferably made of an inner tube catheter 103 and a proximal supporting tube 104. The inner tube catheter 103 is preferably approximately 20 centimeters in length. The inner tube catheter 103 is preferably made of polyethylene. The proximal supporting tube 104 is preferably approximately 10–12 centimeters in length and can be made of a stiffer plastic than the inner tube catheter 103, of the same family but stiffer. The proximal supporting tube 104 is preferably manufactured by adhering an additional sheath of tubing around the most proximal 10–12 centimeters of the inner tube catheter 103. So, the inner catheter 103 is preferably continuous throughout the length of the inner catheter 69, and the proximal supporting tube 104 is preferably a separate length of tube which is attached (as by adhering in well-known ways, preferably near the proximal end 88) in place preferably around the most proximal 10 to 12 centimeters of the inner tube catheter 103. The inner tube catheter 103 and the proximal supporting tube 104 together comprise the inner catheter 69.

The inner diameter of the inner catheter 69 is preferably continuous throughout the length of the inner catheter 69 and is preferably approximately 1 mm in diameter. The outer diameter of the inner tube catheter 103 is preferably approximately 1.5 mm in diameter. The outer diameter of the proximal supporting tube 104 is preferably approximately 2.5 mm (these dimensions/arrangement embodying herein wherein such inner catheter comprises a proximal portion having a larger external diameter than an external diameter of a distal portion of such inner catheter). The inner catheter 103, as noted, is preferably thin and very soft to prevent trauma to the surrounding uterus or to the embryos being transferred. However, it can be difficult for a long soft catheter to push through the end cap 73 of the outer sleeve 68 as described above. The addition of the proximal supporting tube 104 allows the length of inner catheter 103 to be significantly shortened and gives it the strength it needs to push through the outer sleeve 68 and for easier handling by the physician. As described in relation to previous embodiments, the distal end 71 of the inner catheter 69 preferably contains a side opening 105 for the deposit of embryos. As shown if FIG. 23, it is preferred that such proximal portion of such inner catheter is at least as long as such proximal portion of such catheter outer sleeve.

FIG. 27 illustrates a cross-section at section 27—27 of FIG. 23 showing the proximal portion 76 of the outer sleeve 68 containing the proximal supporting tube 104 wrapped around the inner tube catheter 103. The proximal supporting tube 104 preferably slides through the outer sleeve 68 as illustrated in FIG. 27. The proximal supporting tube 104 cannot extend into the distal portion 75 of the outer sleeve 68 because the inner diameter of the distal portion 75 of the outer sleeve 68 is not sufficiently large to accommodate the outer diameter OD7 of the proximal supporting tube 104. This gives the physician a safe stop or block to avoid injury by extending the inner catheter 69 too far into the uterus and also a method for measuring the distance that the inner catheter 69 has traveled through the cervix 26 before depositing the embryos 22 into the uterus 21. The inner catheter 69 is preferably attached at its most proximal end 106 to a Luer lock 107. The Luer lock 107 is preferably attachable to a syringe 108. The Luer lock 107 preferably has a marker 109 which helps indicate to the physician the location of the side-eye opening 105 in the distal end 71 of the inner catheter 69.

The proximal supporting tube 104 serves many purposes in addition to lending strength to the inner catheter 69. In apparatus without the proximal supporting tube 104, the inner catheter 69 attached to a relatively heavy syringe 108 is a very flimsy combination. So, while the physician introduced the outer sleeve 68 through the cervix 26 s/he was required to bend the inner catheter 69 to be able to hold the syringe and the inner catheter 69 in the same hand. Generally, the embryos are loaded into the very tip of the inner catheter 69. Bending the catheter and the heat from the physician's hand required by the direct contact between the hand and the catheter when holding it, may cause a volume change inside the catheter, which may accidentally and prematurely push the embryos out of the tip of the inner catheter 69. Alternatively, the physician may require the assistance of a third hand, which can be awkward. Without supporting tube 104, the physician was required to insert the outer sleeve 68 through the cervix 22. Then, when the outer sleeve 68 was in place, the physician would introduce the inner catheter 69 into the outer sleeve 68. However, pushing a long, thin, soft catheter through the outer sleeve 68 can be very difficult. Throughout this procedure, the physician risks dropping the inner catheter 69 attached to the syringe 108 and damaging the embryos. Also, the weight of the syringe 108 on the end of a long thin catheter may pull the syringe 108 attached to the inner catheter 69 out of the outer sleeve 68 resulting in embryo damage or loss. This preferred embodiment 70, with the proximal supporting tube 104, eases some of these technical difficulties and makes the transfer process easier. Because of the increased rigidity of the supporting tube, the physician can more readily introduce the entire preferred embodiment 70 as one unit, with the inner catheter 69 already placed inside the outer sleeve 68, through the cervix 22. The inner catheter 69 can be placed inside the outer sleeve 68 with the end cap 73 closed so that the inner catheter 69 is protected from mucus or bending by the outer sleeve 68. The portion of the inner catheter 69 which extends beyond the manipulative end 97 of the outer sleeve 68 is stiffened and reinforced by the proximal supporting tube 104 and is strong enough to feel solid and support the weight of the syringe 108. The physician does not need to hold the inner catheter 69 attached to the syringe separately and no third hand is necessary. The risk of dropping the syringe is much lower because the catheter with a syringe is firmly inserted in the outer sleeve 68 and the position is horizontal. The risk of accidentally pushing the embryos out of the catheter are significantly reduced because the inner catheter 69 is kept straight by the outer sleeve 68 and the physician's hand only touches the syringe 108 or the proximal supporting tube 104 and does not come into direct contact with the inner catheter 69. Increasing embryo protection from mucus and increasing the ease with which the physician can perform the procedure will increase the probability of a positive outcome for the patient. Clinical studies using the within inventions (including the described swivelable end cap) for protecting embryos have indicated a better implantation rate and a better pregnancy rate.

The above description taken with the descriptions of FIG. 13 et seq. hereof embody a catheter system for single-person implanting of an embryo in a uterus, comprising, in combination, the steps of: providing a wire-stiffened catheter outer sleeve having a longitudinal cylindrical hollow between a sleeve proximal end and a sleeve distal end, wherein a proximal portion of such cylindrical hollow has a larger internal diameter than an internal diameter of a distal portion of such cylindrical hollow; providing an inner catheter having a catheter proximal end and a catheter distal end having an opening for transmission of a such embryo, such catheter being sized for moving through such longitudinal cylindrical hollow, wherein a proximal portion of such inner catheter has a greater catheter wall thickness than a distal portion of such inner catheter, and wherein such proximal portion of such inner catheter has a larger external diameter than an external diameter of such distal portion of such inner catheter, and such inner catheter being structured and arranged to supportingly fit within such outer sleeve, thereby providing substantially greater catheter system stiffness; affixing a syringe at such proximal end of such inner catheter; loading such embryo into such inner catheter distal end; placing such inner catheter into such proximal end of such outer sleeve and moving such inner catheter forward until such inner catheter distal end is approaching such sleeve distal end; introducing such sleeve proximal end into a cervix to a desired stop location; further moving such inner catheter forward into such end cap of such outer sleeve, outwardly swiveling such end cap, and further moving such catheter distal end forward into access to the uterus to a desired implanting location; and flushing such embryo out of such catheter distal end; and, further, wherein, during such step of further moving such inner catheter forward, forward travel of such inner catheter is limited by a distal end of such proximal portion of such inner catheter being blocked when reaching a distal end of such proximal portion of such outer sleeve, thereby assisting in avoiding injury to the uterus from too much forward travel of such inner catheter; and, further, wherein such step of moving such inner catheter forward may be accomplished by one hand of a catheter system user because of such substantially greater catheter system stiffness.

Although applicant has described applicant's preferred embodiments of this invention, it will be understood that the broadest scope of this invention includes such modifications as diverse shapes and sizes and materials. Such scope is limited only by the below claims as read in connection with the above specification. Further, many other advantages of applicant's invention will be apparent to those skilled in the art from the above descriptions and the below claims.

What is claimed is:

1. A catheter system for implanting embryos in a uterus, the system comprising:
   a. a substantially tubular inner catheter comprising a catheter port positioned proximal a rounded distal catheter end; and
   b. a catheter outer sleeve having a longitudinal cylindrical hollow within the catheter outer sleeve and extending from a sleeve proximal end to a sleeve distal end, the sleeve distal end having a rounded end and a slit in the sleeve distal end extending from an outer surface of the catheter outer sleeve to the cylindrical hollow, the rounded end being hingedly attached to the distal end and normally biased closed against the cylindrical hollow;
   wherein the slit is located at a first location on the distal end proximal a second location on the distal end, the second location having a second outer sleeve external diameter greater than or equal to a first outer sleeve external diameter of the first location; and
   wherein the cylindrical hollow is sized and shaped to receive the inner catheter therethrough, thereby providing catheter access to the uterus by the inner catheter pushing open the normally biased closed rounded end at the slit.

2. The catheter system of claim 1, wherein the rounded distal end of the catheter outer sleeve located distally of the slit comprises a smooth surface and a region of the catheter outer sleeve proximal the slit comprises a rough surface adapted to trap mucus into which the catheter outer sleeve is placed.

3. The catheter system of claim 1, wherein the catheter outer sleeve comprises an internal surface defining the longitudinal cylindrical hollow, wherein an internal surface portion comprises a rough surface.

4. The catheter system of claim 3, wherein the rough surface comprises hair-like protrusions extending from the internal surface.

5. The catheter system of claim 1, wherein a transition between the catheter outer sleeve and the normally closed rounded end is continuous but for the slit, having a diameter which transitions smoothly from the catheter outer sleeve and the rounded distal end of the outer sleeve.

6. The catheter system of claim 1, wherein the rounded distal end of the outer sleeve is a unitary part of the catheter outer sleeve.

7. The catheter system of claim 1, the catheter outer sleeve further having a distal end portion formed of a soft, resilient material, a formable portion coupled to the distal end portion, the formable portion being formed of a material harder than the soft, resilient material, the formable portion having memory such that when the formable portion is manipulated into a position, it substantially retains that position until reformed, the catheter outer sleeve also further having a sleeve supporting portion coupled to the formable portion, the sleeve supporting portion being more rigid than the formable portion.

8. The catheter system of claim 7, wherein the supporting portion is rigid.

9. The catheter system of claim 1, the outer catheter sleeve having a formable portion having memory such that when the formable portion is manipulated into a position, it substantially retains that position until re-formed.

10. The catheter system of claim 9, the outer catheter sleeve further having a wire extending substantially from its proximal end to its distal end, the wire extending inside a wall of the outer catheter sleeve, but outside the longitudinal cylindrical hollow.

11. The catheter system of claim 1, wherein the outer catheter sleeve comprises a proximal sleeve portion having a sleeve first inner diameter and a distal sleeve portion having a sleeve second inner diameter, the distal sleeve portion being distally located from the proximal sleeve portion and beginning at a point approximately 4 cm from the distal end of the outer catheter sleeve;

wherein the inner catheter comprises an inner catheter proximal portion having an inner catheter first outer diameter and an inner catheter distal portion distally located from the inner catheter proximal portion, the inner catheter distal portion having an inner catheter second outer diameter; and wherein the sleeve second inner diameter is larger than the inner catheter second outer diameter and smaller than inner catheter first outer diameter and the sleeve first inner diameter such that the inner catheter is stopped from passing through the outer catheter sleeve when the inner catheter proximal portion contacts the distal sleeve portion.

12. The catheter system of claim 11, wherein the inner catheter comprises a catheter longitudinal cylindrical hollow having an inner catheter diameter substantially constant throughout both the proximal and distal portions of the inner catheter.

13. The catheter system of claim 11, wherein the proximal sleeve portion comprises a proximal sleeve wall thickness greater than a distal sleeve wall thickness of the distal sleeve portion.

14. The catheter system of claim 1, wherein the inner catheter comprises a flexible portion for extending into the uterus, and a supporting catheter portion proximal to the flexible portion, the supporting catheter portion being more resilient than the flexible portion.

15. The catheter system of claim 14, wherein the supporting catheter portion comprises a first catheter wall thickness greater than a second catheter wall thickness of the flexible portion.

16. The catheter system of claim 15, wherein the supporting catheter portion is rigid.

17. The catheter system of claim 1, wherein the slit is at an angle of between approximately 0 to 45 degrees from a reference perpendicular to the catheter outer sleeve.

18. The catheter system of claim 17, wherein the slit is at an angle of between approximately 15 and 20 degrees from the reference.

19. The catheter system of claim 1, further comprising a catheter port orientation indicator on the inner catheter.

20. The catheter system of claim 1, wherein the outer catheter sleeve comprises a proximal sleeve portion and a distal sleeve portion having a bend therein, the outer catheter sleeve further comprising a bend orientation indicator.

21. The catheter system of claim 1, wherein the slit extending from the outer surface of the catheter outer sleeve to the cylindrical hollow extends around at least about 200 degrees of a circumference around the catheter outer sleeve.

22. The catheter system of claim 1, wherein the slit extending from the outer surface of the catheter outer sleeve to the cylindrical hollow partially defines a planar surface adjacent the cylindrical hollow against which the rounded end is biased closed.

23. A catheter system for implanting embryos in a uterus, the system comprising:

a. a substantially tubular inner catheter comprising a catheter port positioned proximal a rounded distal catheter end; and b. a catheter outer sleeve having a longitudinal cylindrical hollow within the outer sleeve and extending from a sleeve proximal end to a sleeve distal end, the sleeve distal end having a rounded end and a slit in the sleeve distal end extending from an outer surface of the catheter outer sleeve to the cylindrical hollow, the rounded end being hingedly attached to the distal end and normally biased closed against the cylindrical hollow;

wherein the rounded distal end of the catheter outer sleeve located distally of the slit comprises a smooth surface and a region of the catheter outer sleeve proximal the slit comprises a rough surface adapted to trap mucus into which the catheter outer sleeve is placed; and wherein the cylindrical hollow is sized and shaped to receive the inner catheter therethrough, thereby providing catheter access to the uterus by the inner catheter pushing open the normally closed rounded end at the slit.

24. The catheter system of claim 23, the catheter outer sleeve comprises an internal surface defining the longitudinal cylindrical hollow, wherein an internal surface portion comprises a rough surface.

25. The catheter system of claim 24, wherein the rough surface comprises hair-like protrusions extending from the internal surface.

26. The catheter system of claim 23, wherein a transition between the catheter outer sleeve and the normally closed rounded end is continuous but for the slit, having a diameter which transitions smoothly from the catheter outer sleeve and the rounded distal end of the outer sleeve.

27. The catheter system of claim 23, wherein the rounded distal end of the outer sleeve is a unitary part of the catheter outer sleeve.

28. The catheter system of claim 23, the catheter outer sleeve further having a distal end portion formed of a soft, resilient material, a formable portion coupled to the distal end portion, the formable portion being formed of a material harder than the soft, resilient material, the formable portion having memory such that when the formable portion is manipulated into a position, it substantially retains that position until re-formed, the catheter outer sleeve also further having a sleeve supporting portion coupled to the formable portion, the sleeve supporting portion being more rigid than the formable portion.

29. The catheter system of claim 28, wherein the supporting portion is rigid.

30. The catheter system of claim 23, the outer catheter sleeve having a formable portion having memory such that when the formable portion is manipulated into a position, it substantially retains that position until re-formed.

31. The catheter system of claim 30, the outer catheter sleeve further having a wire extending substantially from its proximal end to its distal end, the wire extending inside a wall of the outer catheter sleeve, but outside the longitudinal cylindrical hollow.

32. The catheter system of claim 23, wherein the outer catheter sleeve comprises a proximal sleeve portion having a sleeve first inner diameter and a distal sleeve portion having a sleeve second inner diameter, the distal sleeve portion being distally located from the proximal sleeve portion and beginning at a point approximately 4 cm from the distal end of the outer catheter sleeve;

wherein the inner catheter comprises an inner catheter proximal portion having an inner catheter first outer diameter and an inner catheter distal portion distally located from the inner catheter proximal portion, the inner catheter distal portion having an inner catheter second outer diameter; and wherein the sleeve second inner diameter is larger than the inner catheter second outer diameter and smaller than inner catheter first outer diameter and the sleeve first inner diameter such that the inner catheter is stopped from passing through the outer catheter sleeve when the inner catheter proximal portion contacts the distal sleeve portion.

33. The catheter system of claim 32, wherein the inner catheter comprises a catheter longitudinal cylindrical hollow having an inner catheter diameter substantially constant throughout both the proximal and distal portions of the inner catheter.

34. The catheter system of claim 32, wherein the proximal sleeve portion comprises a proximal sleeve wall thickness greater than a distal sleeve wall thickness of the distal sleeve portion.

35. The catheter system of claim 23, wherein the inner catheter comprises a flexible portion for extending into the uterus, and a supporting catheter portion proximal to the flexible portion, the supporting catheter portion being more resilient than the flexible portion.

36. The catheter system of claim 35, wherein the supporting catheter portion comprises a first catheter wall thickness greater than a second catheter wall thickness of the flexible portion.

37. The catheter system of claim 35, wherein the supporting catheter portion is rigid.

38. The catheter system of claim 23, wherein the slit is at an angle of between approximately 0 to 45 degrees from a reference perpendicular to the catheter outer sleeve.

39. The catheter system of claim 23, further comprising a catheter port orientation indicator on the inner catheter.

40. The catheter system of claim 23, wherein the outer catheter sleeve comprises a proximal sleeve portion and a distal sleeve portion having a bend therein, the outer catheter sleeve further comprising a bend orientation indicator.

41. The catheter system of claim 23, wherein the slit extending from the outer surface of the catheter outer sleeve to the cylindrical hollow extends around at least about 200 degrees of a circumference around the catheter outer sleeve.

42. The catheter system of claim 23, wherein the slit extending from the outer surface of the catheter outer sleeve to the cylindrical hollow partially defines a planar surface adjacent the cylindrical hollow against which the rounded end is biased closed.

43. A catheter system for implanting embryos in a uterus, the system comprising:
   a. a substantially tubular inner catheter comprising a catheter port positioned proximal a rounded distal catheter end; and
   b. a catheter outer sleeve having a longitudinal cylindrical hollow within the outer sleeve and extending from a sleeve proximal end to a sleeve distal end, the sleeve distal end having a rounded end normally biased closed against the cylindrical hollow, the catheter outer sleeve further having a slit in the sleeve distal end extending from an outer surface of the catheter outer sleeve to the cylindrical hollow, wherein a transition between the catheter outer sleeve and the normally closed rounded end is continuous but for the slit, having a diameter which transitions smoothly from the catheter outer sleeve and the rounded distal end of the outer sleeve;
      wherein the cylindrical hollow is sized and shaped to receive the inner catheter therethrough for providing catheter access to the uterus by the inner catheter pushing open the normally closed rounded end at the slit.

44. The catheter system of claim 43, wherein the rounded distal end of the catheter outer sleeve located distally of the slit comprises a smooth surface and a region of the catheter outer sleeve proximal the slit comprises a rough surface adapted to trap mucus into which the catheter outer sleeve is placed.

45. The catheter system of claim 43, wherein the catheter outer sleeve comprises an internal surface defining the longitudinal cylindrical hollow, wherein an internal surface portion comprises a rough surface.

46. The catheter system of claim 45, wherein the rough surface comprises hair-like protrusions extending from the internal surface.

47. The catheter system of claim 43, wherein the rounded distal end of the outer sleeve is a unitary part of the catheter outer sleeve.

48. The catheter system of claim 43, the catheter outer sleeve further having a distal end portion formed of a soft, resilient material, a formable portion coupled to the distal end portion, the formable portion being formed of a material harder than the soft, resilient material, the formable portion having memory such that when the formable portion is manipulated into a position, it substantially retains that position until reformed, the catheter outer sleeve also further having a sleeve supporting portion coupled to the formable portion, the sleeve supporting portion being more rigid than the formable portion.

49. The catheter system of claim 43, the outer catheter sleeve having a formable portion having memory such that when the formable portion is manipulated into a position, it substantially retains that position until re-formed.

50. The catheter system of claim 49, the outer catheter sleeve further having a wire extending substantially from its proximal end to its distal end, the wire extending inside a wall of the outer catheter sleeve, but outside the longitudinal cylindrical hollow.

51. The catheter system of claim 43, wherein the outer catheter sleeve comprises a proximal sleeve portion having a sleeve first inner diameter and a distal sleeve portion having a sleeve second inner diameter, the distal sleeve portion being distally located from the proximal sleeve portion and beginning at a point approximately 4 cm from the distal end of the outer catheter sleeve;
   wherein the inner catheter comprises an inner catheter proximal portion having an inner catheter first outer diameter and an inner catheter distal portion distally located from the inner catheter proximal portion, the inner catheter distal portion having an inner catheter second outer diameter; and
   wherein the sleeve second inner diameter is larger than the inner catheter second outer diameter and smaller than inner catheter first outer diameter and the sleeve first inner diameter such that the inner catheter is stopped from passing through the outer catheter sleeve when the inner catheter proximal portion contacts the distal sleeve portion.

52. The catheter system of claim 48, wherein the inner catheter comprises a catheter longitudinal cylindrical hollow having an inner catheter diameter substantially constant throughout both the proximal and distal portions of the inner catheter.

53. The catheter system of claim 48, wherein the proximal sleeve portion comprises a proximal sleeve wall thickness greater than a distal sleeve wall thickness of the distal sleeve portion.

54. The catheter system of claim 43, wherein the inner catheter comprises a flexible portion for extending into the uterus, and a supporting catheter portion proximal to the flexible portion, the supporting catheter portion being more resilient than the flexible portion.

55. The catheter system of claim 51, wherein the supporting catheter portion comprises a first catheter wall thickness greater than a second catheter wall thickness of the flexible portion.

56. The catheter system of claim 43, wherein the slit extending from the outer surface of the catheter outer sleeve to the cylindrical hollow partially defines a planar surface adjacent the cylindrical hollow against which the rounded end is biased closed.

57. A catheter system for implanting embryos in a uterus, comprising:
 a. a substantially tubular inner catheter comprising a catheter port positioned proximal a rounded distal catheter end; and
 b. a catheter outer sleeve having a longitudinal cylindrical hollow within the catheter outer sleeve and extending from a sleeve proximal end to a sleeve distal end, the sleeve distal end having a rounded end and a slit in the sleeve distal end extending from an outer surface of the catheter outer sleeve to the cylindrical hollow, the rounded end being hingedly attached to the distal end and normally biased closed against the cylindrical hollow, the outer catheter sleeve further having a channel separate from but adjacent to the longitudinal cylindrical hollow within a wall of the catheter outer sleeve, the channel housing a wire extending substantially from the sleeve proximal end to the sleeve distal end;
 wherein the cylindrical hollow is sized and shaped to receive the inner catheter therethrough, thereby providing catheter access to the uterus by the inner catheter pushing open the normally biased closed rounded end at the slit.

58. The catheter system of claim 54, the catheter outer sleeve further having a distal end portion formed of a soft, resilient material, a formable portion coupled to the distal end portion, the formable portion being formed of a material harder than the soft, resilient material, the formable portion having memory such that when the formable portion is manipulated into a position, it substantially retains that position until reformed, the catheter outer sleeve also further having a sleeve supporting portion coupled to the formable portion, the sleeve supporting portion being more rigid than the formable portion.

59. The catheter system of claim 55, wherein the sleeve supporting portion is rigid.

60. The catheter system of claim 54, the outer catheter sleeve having a formable portion having memory such that when the formable portion is manipulated into a position, it substantially retains that position until re-formed.

61. The catheter system of claim 57, the outer catheter sleeve further having a wire extending substantially from its proximal end to its distal end, the wire extending inside a wall of the outer catheter sleeve, but outside the longitudinal cylindrical hollow.

62. The catheter system of claim 54, wherein the outer catheter sleeve comprises a proximal sleeve portion having a sleeve first inner diameter and a distal sleeve portion having a sleeve second inner diameter, the distal sleeve portion being distally located from the proximal sleeve portion and beginning at a point approximately 4 cm from the distal end of the outer catheter sleeve;
 wherein the inner catheter comprises an inner catheter proximal portion having an inner catheter first outer diameter and an inner catheter distal portion distally located from the inner catheter proximal portion, the inner catheter distal portion having an inner catheter second outer diameter; and
 wherein the sleeve second inner diameter is larger than the inner catheter second outer diameter and smaller than inner catheter first outer diameter and the sleeve first inner diameter such that the inner catheter is stopped from passing through the outer catheter sleeve when the inner catheter proximal portion contacts the distal sleeve portion.

63. The catheter system of claim 59, wherein the proximal sleeve portion comprises a proximal sleeve wall thickness greater than a distal sleeve wall thickness of the distal sleeve portion.

64. The catheter system of claim 54, wherein the inner catheter comprises a flexible portion for extending into the uterus, and a supporting catheter portion proximal to the flexible portion, the supporting catheter portion being more resilient than the flexible portion.

65. The catheter system of claim 64, wherein the supporting catheter portion comprises a first catheter wall thickness greater than a second catheter wall thickness of the flexible portion.

66. The catheter system of claim 54, wherein the slit is at an angle of between approximately 0 to 45 degrees from a reference perpendicular to the catheter outer sleeve.

67. The catheter system of claim 66, wherein the slit is at an angle of between approximately 15 and 20 degrees from the reference.

68. A catheter system for implanting embryos in a uterus, the system comprising:
 a. a substantially tubular inner catheter comprising a catheter port positioned proximal a rounded distal catheter end; and
 b. a catheter outer sleeve having a longitudinal cylindrical hollow within the catheter outer sleeve and extending from a sleeve proximal end to a sleeve distal end, the sleeve distal end having a rounded end and a slit in the sleeve distal end extending from an outer surface of the catheter outer sleeve to the cylindrical hollow, the rounded end being hingedly attached to the distal end and normally biased closed against the cylindrical hollow;
 wherein the outer catheter sleeve comprises a proximal sleeve portion having a sleeve first inner diameter and a distal sleeve portion having a sleeve second inner diameter, the distal sleeve portion being distally located from the proximal sleeve portion;
 wherein the inner catheter comprises an inner catheter proximal portion having an inner catheter first outer diameter and an inner catheter distal portion distally located from the inner catheter proximal portion, the inner catheter distal portion having an inner catheter second outer diameter; and
 wherein the sleeve second inner diameter is larger than the inner catheter second outer diameter and smaller than inner catheter first outer diameter and the sleeve first inner diameter such that the inner catheter is stopped from passing through the outer catheter sleeve when the inner catheter proximal portion contacts the distal sleeve portion.

69. The catheter system of claim 68, wherein the proximal sleeve portion comprises a proximal sleeve wall thickness greater than a distal sleeve wall thickness of the distal sleeve portion.

\* \* \* \* \*